United States Patent
Bandman et al.

(12) 
(10) Patent No.: US 6,303,765 B1
(45) Date of Patent: Oct. 16, 2001

(54) HUMAN EXTRACELLULAR MATRIX PROTEINS

(75) Inventors: Olga Bandman; Neil C. Corley, both of Mountain View; Karl J. Guegler, Menlo Park, all of CA (US)

(73) Assignee: Incyte Genomics, Inc., Palo Alto, CA (US)

(*) Notice: Subject to any disclaimer, the term of this patent is extended or adjusted under 35 U.S.C. 154(b) by 0 days.

(21) Appl. No.: 09/212,168

(22) Filed: Dec. 15, 1998

Related U.S. Application Data

(62) Division of application No. 08/884,072, filed on Jun. 27, 1997, now Pat. No. 5,872,234.

(51) Int. Cl.$^7$ .................................................. C07H 21/02
(52) U.S. Cl. ...................... 536/23.1; 435/71.1; 435/69.1; 435/320.1
(58) Field of Search ........................... 536/23.1; 435/69.1, 435/71.1, 320.1; 530/350

(56) References Cited

FOREIGN PATENT DOCUMENTS

| 22623 | * 6/1997 | (WO) . |
| WO 97/38002 | 10/1997 | (WO) . |
| WO 97/39122 | 10/1997 | (WO) . |
| WO 97/39123 | 10/1997 | (WO) . |
| 98/31798 | 7/1998 | (WO) . |

OTHER PUBLICATIONS

Database Geneseq, Accession No. T22250, 1995.*
Database embl–est58, Accession No. AA306096, Apr. 1997.*
Database embl–est58, Accession No. R83319, Aug. 1995.*
Database embl58, Accession No. U65932, Aug. 1996.*
Database EMBL Nucleotide and Protein Sequences, Oct. 1, 1998, XP002086216, Hinxton, GB AC—AF093118.
McGowan, S.E., "Extracellular matrix and the regulation of lung development and repair", *FASEB J*, 6(11): 2895–2904 (1992).
Grant, D.S., et al., "Regulation of capillary formation by laminin and other components of the extracellular matrix", *EXS* 79: 317–333 (1997).
Taipale, J., et al., "Growth factors in the extracellular matrix", *FASEB J*, 11 (1): 51–59 (1997).
Eleftheriou, C.S., et al., "Cellular ageing related proteins secreted by human fibroblasts", *Mutat Res.*, 256 (2–6): 127–138 (1991).
Francomano, C.A., et al., "Bone dysplasias in man: molecular insights" *Curr Opin Genet Dev*, 6(3): 301–308 (1996).

Pakianathan, D.R., "Extracellular matrix proteins and leukocyte function", *J. Leukoc Biol*, 57(5): 699–702 (1995).
Roman, J., "Extracellular matrix and lung inflammation", *Immunol Res*, 15(2): 163–178 (1996).
Lecka–Czernik, B., et al., "An overexpressed gene transcript in senescent and quiescent human fibroblasts encoding a novel protein in the epidermal growth factor–like repeat family stimulates DNA synthesis", *Mol Cell Biol*, 15(1): 120–128 (1995). (458228).
Bhalerao, J., et al., "Molecular Cloning, Characterization, and Genetic Mapping of the cDNA Coding for a Novel Secretory Protein of Mouse", *The Journal of Biological Chemistry*, 270(27): 16385–16394 (1995). (496120).
Soltysik–Espanola, M., et al., "Endo16, a large multidomain protein found on the surface and ECM of endodermal cells during sea urchin gastrulation, binds calcium", *Dev Biol*, 165(1): 73–85 (1994).
Kragh–Hansen, U., "Structure and ligand binding properties of human serum albumin", *Dan Med Bull*, 37(1): 57–84 (1990).
Chiquet–Ehrismann, R., et al., "Tenascin: an Extracellular Matrix Protein Involved in Tissue Interactions during Fetal Development and Oncogenesis", *Cell*, 47: 131–139 (1986).
Johnson, M.R., et al., (GI 1488323) GenBank Sequence Database (Accession U65932), National Center for Biotechnology Information: National Library of Medicine, Bethesda, Maryland 20849 (1996).
Lecka–Czernick, B., (GI 458227) GenBank Sequence Database (Accession U03877), National Center for Biotechnology Information: National Library of Medicine, Bethesda, Maryland 20849 (1995).
Bhalerao, J., et al., (GI 496119) GenBank Sequence Database (Accession L33416), National Center for Biotechnology Information: National Library of Medicine, Bethesda, Maryland 20849 (1994).
Hillier, L. et al., Database Genbank, subsection EST Accession No. N50529 (1996).
Hillier, L. et al., Database Genbank, subsection EST Accession No. AA035381 (1996).
Hillier, L. et al., Database Genbank, subsection EST Accession, No. W78139 (1996).
Hillier, L. et al., Database Genbank, subsection EST Accession No. W19260 (1996).

* cited by examiner

*Primary Examiner*—Sheela Huff
(74) *Attorney, Agent, or Firm*—Incyte Genomics, Inc.

(57) ABSTRACT

The invention provides two human extracellular matrix proteins (ECMP) and polynucleotides which identify and encode ECMP. The invention also provides expression vectors, host cells, agonists, antibodies and antagonists. The invention also provides methods for treating disorders associated with expression of ECMP.

15 Claims, 17 Drawing Sheets

```
          9              18          27          36          45          54
5' CCA AGA TTG TTG TGA GGA GTC TAG CCA GTT GGT GAG CGC TGT AAT CTG AAC CAG 63             72          81          90          99         108
CTG TGT CCA GAC TGA GGC CCC ATT TGC ATT ATT TAA CAT ACT TAG AAA ATG AAG 117           126         135         144         153         162
TGT TCA TTT TTA ACA TTC CTC CTC CAA TTG GTT TAA TGC TGA ATT ACT GAA GAG 171           180         189         198         207         216
GGC TAA GCA AAA CCA GGT GCT TGC GCT GAG GGC TCT GCA GTG GCT GGG AGG ACC 225           234         243         252         261         270
CCG GCG CTC TCC CCG TGT CCT CTC CAC GAC TCG CTC GGC CCC TCT GGA ATA AAA 279           288         297         306         315         324
CAC CCG CGA GCC CCG AGG GCC CAG AGG AGG CCG ACG TGC CCG AGC TCC TCC GGG 333           342         351         360         369         378
GGT CCC GCC CGC GAG CTT TCT TCT CGC CTT CGC ATC TCC TCC TCG CGC GTC TTG 387           396         405         414         423         432
GAC ATG CCA GGA ATA AAA AGG ATA CTC ACT GTT ACC ATT CTG GCT CTC TGT CTT
     M   P   G   I   K   R   I   L   T   V   T   I   L   A   L   C   L
```

FIGURE 1A

```
     441            450       459       468       477       486
CCA  AGC  CCT  GGG  AAT  GCA  CAG  GCA  TGC  ACG  AAT  GGC  TTT  GAC  CTG  GAT  CGC
 P    S    P    G    N    A    Q    A    Q    C    T    N    G    F    D    L    D    R 495            504       513       522       531       540
CAG  TCA  GGA  CAG  TGT  TTA  GAT  ATT  GAT  GAA  TGC  CGA  ACC  ATC  CCC  GAG  GCC  TGC
 Q    S    G    Q    C    L    D    I    D    E    C    R    T    I    P    E    A    C 549            558       567       576       585       594
CGA  GGA  GAC  ATG  ATG  TGT  GTT  AAC  CAA  AAT  GGC  GGG  TAT  TTA  TGC  ATT  CCC  CGG
 R    G    D    M    M    C    V    N    Q    N    G    G    Y    L    C    I    P    R 603            612       621       630       639       648
ACA  AAC  CCT  GTG  TAT  CGA  GGG  CCC  TAC  TCG  AAC  CCC  TAC  TCG  ACC  CCC  TAC  TCA
 T    N    P    V    Y    R    G    P    Y    S    N    P    Y    S    T    P    Y    S 657            666       675       684       693       702
GGT  CCG  TAC  CCA  GCA  GCT  GCC  CCA  CTC  TCA  GCT  CCA  AAC  TAT  CCC  ACG  ATC
 G    P    Y    P    A    A    A    P    L    S    A    P    N    Y    P    T    I 711            720       729       738       747       756
TCC  AGG  CCT  CTT  ATA  TGC  CGC  TTT  GGA  TAC  CAG  ATG  GAT  GAA  AGC  AAC  CAA  TGT
 S    R    P    L    I    C    R    F    G    Y    Q    M    D    E    S    N    Q    C 765            774       783       792       801       810
GTG  GAT  GTG  GAC  GAG  TGT  GCA  ACA  GAT  TCC  CAC  CAG  TGC  AAC  CCC  ACC  CAG  ATC
 V    D    V    D    E    C    A    T    D    S    H    Q    C    N    P    T    Q    I

FIGURE 1B
```

```
      819                 828                 837                 846                 855                 864
TGC ATC AAT ACT GAA GGC GGG TAC ACC TGC TCC TGC ACC GAC GGA TAT TGG CTT
 C   I   N   T   E   G   G   Y   T   C   S   C   T   D   G   Y   W   L 873                 882                 891                 900                 909                 918
CTG GAA GGC CAG TGC TTA GAC ATT GAT GAA TGT CGC TAT CGC TAT TGC CAG CAG
 L   E   G   Q   C   L   D   I   D   E   C   R   Y   R   Y   C   Q   Q 927                 936                 945                 954                 963                 972
CTC TGT GCG AAT GTT CCT GGA TCC TAT TCT TGT ACA TGC AAC CCT GGT TTT ACC
 L   C   A   N   V   P   G   S   Y   S   C   T   C   N   P   G   F   T 981                 990                 999                1008                1017                1026
CTC AAT GAG GAT GGA AGG TCT TGC CAA GAT GTG AAC GAG TGT GCC ACC GAG AAC
 L   N   E   D   G   R   S   C   Q   D   V   N   E   C   A   T   E   N 1035                1044                1053                1062                1071                1080
CCC TGC GTG CAA ACC TGC GTC AAC ACC TAC GGC TCT TTC ATC TGC CGC TGT GAC
 P   C   V   Q   T   C   V   N   T   Y   G   S   F   I   C   R   C   D 1089                1098                1107                1116                1125                1134
CCA GGA TAT GAA CTT GAG GAA GAT GGC GTT CAT CAT TGC AGT GAT ATG GAC GAG TGC
 P   G   Y   E   L   E   E   D   G   V   H   H   C   S   D   M   D   E   C 1143                1152                1161                1170                1179                1188
AGC TTC TCT GAG TTC CTC TGC CAA CAT GAG TGT GTG AAC CAG CCC GGC ACA TAC
 S   F   S   E   F   L   C   Q   H   E   C   V   N   Q   P   G   T   Y
```

FIGURE 1C

```
      1197            1206            1215            1224            1233            1242
TTC TGC TCC TGC CCT CCA GGC TAC ATC CTG CTG GAT GAC AAC CGA AGC TGC CAA
 F   C   S   C   P   P   G   Y   I   L   L   D   D   N   R   S   C   Q 1251            1260            1269            1278            1287            1296
GAC ATC AAC GAA TGT GAG CAC AGG AAC CAC ACG TGC AAC CTG CAG CAG ACG TGC
 D   I   N   E   C   E   H   R   N   H   T   C   N   L   Q   Q   T   C 1305            1314            1323            1332            1341            1350
TAC AAT TTA CAA GGG GGC TTC AAA TGC ATC GAC CCC ATC CGC TGT GAG GAG CCT
 Y   N   L   Q   G   G   F   K   C   I   D   P   I   R   C   E   E   P 1359            1368            1377            1386            1395            1404
TAT CTG AGG ATC AGT GAT AAC CGC TGT ATG TGT CCT GCT GAG AAC CCT GGC TGC
 Y   L   R   I   S   D   N   R   C   M   C   P   A   E   N   P   G   C 1413            1422            1431            1440            1449            1458
AGA GAC CAG CCC TTT ACC ATC TTG TAC CGG GAC ATG GAC GTG TCA GGA CGC
 R   D   Q   P   F   T   I   L   Y   R   D   M   D   V   S   G   R 1467            1476            1485            1494            1503            1512
TCC GTT CCC GCT GAC ATC TTC CAA ATG CAA GCC ACG ACC CGC TAC CCT GGG GCC
 S   V   P   A   D   I   F   Q   M   Q   A   T   T   R   Y   P   G   A 1521            1530            1539            1548            1557            1566
TAT TAC ATT TTC CAG ATC AAA TCT GGG AAT GAG GGC AGA GAA TTT TAC ATG CGG
 Y   Y   I   F   Q   I   K   S   G   N   E   G   R   E   F   Y   M   R
```

FIGURE 1D

```
      1575            1584            1593            1602            1611            1620
CAA ACG GGC CCC ATC AGT GCC ACC CTG GTG ATG ACA CGC CCC ATC AAA GGG CCC
 Q   T   G   P   I   S   A   T   L   V   M   T   R   P   I   K   G   P 1629            1638            1647            1656            1665            1674
CGG GAA ATC CAG CTG GAC TTG GAA ATG ATC ACT GTC AAC ACT GTC ATC AAC TTC
 R   E   I   Q   L   D   L   E   M   I   T   V   N   T   V   I   N   F 1683            1692            1701            1710            1719            1728
AGA GGC AGC TCC GTG ATC CGA CTG CGG ATA TAT GTG TCG CAG TAC CCA TTC TGA
 R   G   S   S   V   I   R   L   R   I   Y   V   S   Q   Y   P   F 1737            1746            1755            1764            1773            1782
GCC TCG GGC TGG AGC CTC CGA CGC TGC CTC TCA TTG GCA CCA AGG GAC AGG AGA 1791            1800            1809            1818            1827            1836
AGA GAG AAA ATA ACA GAG AGA ATG AGA GCG ACA CAG ACG TTA GGC ATT TCC TGC 1845            1854            1863            1872            1881            1890
TGA ACG TTT CCC CGA AGA GTC AGC AGC CCC GAC TTC CTG ACT CTC ACC TGT ACT ATT 1899            1908            1917            1926            1935            1944
GCA GAC CTG TCA CCC TGC AGG ACT TGC CAC CCC CAG TTC CTA TGA CAC AGT TAT 1953            1962            1971            1980            1989            1998
CAA AAA GTA TTA TCA TTG CTC CCC TGA TAG AAG ATT GTT GGT GAA TTT TCA AGG
```

FIGURE 1E

```
        2007            2016            2025            2034            2043            2052
CCT TCA GTT TAT TTC CAC TAT TTT CAA AGA AAA TAG ATT AGG TTT GCG GGG GTC
        2061            2070            2079            2088            2097            2106
TGA GTC TAT GTT CAA AGA CTG TGA ACA GCT TGC TGT CAC TTC TTC ACC TCT TCC
        2115            2124            2133            2142            2151            2160
ACT CCT TCT CTC ACT GTG TTA CTG CTT TGC AAA GAC CCG GGA GCT GGC GGG GAA
        2169            2178            2187            2196            2205            2214
CCC TGG GAG TAG CTA GTT TGC TTT TTG CGT ACA CAG AGA AGG CTA TGT AAA CAA
        2223            2232            2241            2250            2259            2268
ACC ACA GCA GGA TCG AAG GGT TTT TAG AGA ATG TGT TTC AAA ACC ATG CCT GGT
        2277            2286            2295            2304            2313            2322
ATT TTC AAC CAT AAA AGA AGT TTC AGT TGT CCT TAA ATT TGT ATA ACG GTT TAA
        2331            2340            2349            2358            2367            2376
TTC TGT CTT GTT CAT TTT GAG TAT TTT TAA AAA ATA TGT CGT AGA ATT CCT TCG
        2385            2394            2403            2412            2421            2430
AAA GGC CTT CAG ACA CAT GCT ATG TTC TGT CTT CCC AAA CCC AGT CTC CTC TCC
        2439            2448            2457            2466            2475            2484
ATT TTA GCC CAG TGT TTT CTT TGA GGA CCC CTT AAT CTT GCT TTC TTT AGA ATT
```

FIGURE 1F

```
     2493           2502           2511           2520           2529           2538
TTT ACC CAA TTG GAT TGG AAT GCA GAG GTC TCC AAA CTG ATT AAA TAT TTG AAG

2547
AGA AAA AAA AAA  3'
```

FIGURE 1G

```
5'  TG GGT GCA AGC TCA CAA CCG TAA CAG CCA CCA GAC AAG CTT CAG TGG CCG GCC
       9        18          27          36          45          54

CTT CAC ATC CAG ACT TGC CTG AGA GGA CCC ACC TCT GAG TGT CCA GTG GTC AGT
     63          72          81          90          99         108

TGC CCC AGG ATG GGG ACC ACA GCC AGA GCA GCC TTG GTC TTG ACC TAT TTG GCT
    117         126         135         144         153         162
                 M   G   T   T   A   R   A   A   L   V   L   T   Y   L   A

GTT GCT TCT GCT GCC TCT GAG GGA CAA GAA GTT GGC TTC ACG GCT ACA GGA CTG
    171         180         189         198         207         216
     V   A   S   A   A   S   E   G   Q   E   V   G   F   T   A   T   G   L

AGG CCA GAG CAC TTT CAA GAA CAC TTT CAA GAA GCT TAC GCA GCT CCC CCA CCC CTA
    225         234         243         252         261         270
     R   P   E   H   F   Q   E   V   G   Y   A   A   P   P   P   L

TCC CGA AGC CTC CCC ATG GAT CAC CCT GAC TCC TCT CAG CAT GGC CCT CCC TTT
    279         288         297         306         315         324
     S   R   S   L   P   M   D   H   P   D   S   S   Q   H   G   P   P   F

GAG CAG AGT CAA GTG CAG CCC CCT CCC TCT CAG GAG GCC ACC CCT CTC CAA
    333         342         351         360         369         378
     E   Q   S   Q   V   Q   P   P   P   S   Q   E   A   T   P   L   Q
```

FIGURE 2A

```
      387                396      405              414          423              432
CAG GAA AAG CTG CTA CCT GCC CAA CTC CCT GCT GAA AAG GAA GTG GGT CCC CCT
 Q   E   K   L   L   P   A   Q   L   P   A   E   K   E   V   G   P   P 441                450      459              468          477              486
CTC CCT CAG GAA GCT GTC CCC CTC CAA AAA GAG CTG CCC TCT CTC CAG CAC CCC
 L   P   Q   E   A   V   P   L   Q   K   E   L   P   S   L   Q   H   P 495                504      513              522          531              540
AAT GAA CAG AAG GAA GGA ATG CCA GCT CCA TTT GGG GAC CAG AGC CAT CCA GAA
 N   E   Q   K   E   G   M   P   A   P   F   G   D   Q   S   H   P   E 549                558      567              576          585              594
CCT GAG TCC TGG AAT GCA GCC CAG TTC CAC TGC CAA GAC CGG CCT TCT CAA GGG GGC
 P   E   S   W   N   A   A   Q   F   H   C   Q   D   R   P   S   Q   G   G 603                612      621              630          639              648
TGG GGC CAC CGG CTG GAT GGC TTT CCC AAC CGT GGG CGG CCT TCT CCA GAC AAT CTG
 W   G   H   R   L   D   G   F   P   N   R   G   R   P   S   P   D   N   L 657                666      675              684          693              702
AAC CAA ATC TGC CTT CCT AAC CTC CAG CAT GTG GTA TAT GGT CCC TGG AAC CTA
 N   Q   I   C   L   P   N   L   Q   H   V   V   Y   G   P   W   N   L 711                720      729              738          747              756
CCA CAG TCC AGC TAC TCC CAC CTC ACT CGC CAG GGT GAG ACC CTC AAT TTC CTG
 P   Q   S   S   Y   S   H   L   T   R   Q   G   E   T   L   N   F   L
```

FIGURE 2B

```
       765            774            783            792            801            810
GAG ATT GGA TAT TCC CGC TGC TGC CAC TGC CGC AGC CAC ACA AAC CGC CTA GAG
 E   I   G   Y   S   R   C   C   H   C   R   S   H   T   N   R   L   E 819            828            837            846            855            864
TGT GCC AAA CTT GTG TGG GAG GAA GCA ATG AGC CGA TTC TGT GAG GCC GAG TTC
 C   A   K   L   V   W   E   E   A   M   S   R   F   C   E   A   E   F 873            882            891            900            909            918
TCG GTC AAG ACC CGA CCC CAC TGG TGC ACG TGC CGG CAG GGG GAG GCT CGG TTC
 S   V   K   T   R   P   H   W   C   T   C   R   Q   G   E   A   R   F 927            936            945            954            963            972
TCC TGC TTC CAG GAG GAA GCT CCC CAG CCA CAC TAC CAG CTC CGG GCC TGC CCC
 S   C   F   Q   E   E   A   P   Q   P   H   Y   Q   L   R   A   C   P 981            990            999           1008           1017           1026
AGC CAT CAG CCT GAT ATT TCC TCG GGT CTT GAG CTG CCT TTC CCT GGG GTG
 S   H   Q   P   D   I   S   S   G   L   E   L   P   F   P   G   V 1035           1044           1053           1062           1071           1080
CCC ACA TTG GAC AAT ATC AAG AAC ATC TGC CAC CTG AGG CGC TTC CGC TCT GTG
 P   T   L   D   N   I   K   N   I   C   H   L   R   R   F   R   S   V 1089           1098           1107           1116           1125           1134
CCA CGC AAC CTG CCA GCT ACT GAC CCC CTA CAA AGG GAG CTG CTG GCA CTG ATC
 P   R   N   L   P   A   T   D   P   L   Q   R   E   L   L   A   L   I

FIGURE 2C
```

```
     1143              1152              1161              1170              1179              1188
CAG CTG GAG AGG GAG TTC CAG CGC TGC TGC CGC CAG GGG AAC AAT CAC ACC TGT
 Q   L   E   R   E   F   Q   R   C   C   R   Q   G   N   N   H   T   C 1197              1206              1215              1224              1233              1242
ACA TGG AAG GCC TGG GAG GAT ACC CTT GCT GAC AAA TAC TGT GAC CGG GAG TAT GCT
 T   W   K   A   W   E   D   T   L   A   D   K   Y   C   D   R   E   Y   A 1251              1260              1269              1278              1287              1296
GTG AAG ACC CAC CAC CAC TTG TGT TGC CGC CAC CCT CCC AGC CCT ACT CGG GAT
 V   K   T   H   H   H   L   C   C   R   H   P   P   S   P   T   R   D 1305              1314              1323              1332              1341              1350
GAG TGC TTT GCC CGT CGG GCT CCT TAC CCC AAC TAT GAC CGG ATC TTG ACC
 E   C   F   A   R   R   A   P   Y   P   N   Y   D   R   I   L   T 1359              1368              1377              1386              1395              1404
ATT GAC ATC GGT CGA GTC ACC CCC AAC CTC ATG GGC CAC CTC TGT GGA AAC CAA
 I   D   I   G   R   V   T   P   N   L   M   G   H   L   C   G   N   Q 1413              1422              1431              1440              1449              1458
AGA GTT CTC ACC AAG CAT AAA CAT ATT CCT GGG CTG ATC CAC AAC ATG ACT GCC
 R   V   L   T   K   H   K   H   I   P   G   L   I   H   N   M   T   A 1467              1476              1485              1494              1503              1512
CGC TGC TGT GAC CTG CCA TTT CCA GAA CAG GCC TGT GCA GAG GAG GAG AAA
 R   C   C   D   L   P   F   P   E   Q   A   C   A   E   E   E   K
```

FIGURE 2D

```
           1521            1530            1539            1548            1557            1566
TTA ACC TTC ATC AAT GAT CTG TGT GGT CCC CGA CGT AAC ATC TGG CGA GAC CCT
 L   T   F   I   N   D   L   C   G   P   R   R   N   I   W   R   D   P 1575            1584            1593            1602            1611            1620
GCC CTC TGC TGT TAC CTG AGT CCT GGG GAT GAA CAG GTC AAC TGC TTC AAC ATC
 A   L   C   C   Y   L   S   P   G   D   E   Q   V   N   C   F   N   I 1629            1638            1647            1656            1665            1674
AAT TAT CTG AGG AAC GTG GCT CTA GTG TCT GGA GAC ACT GAG AAC GCC AAG GGC
 N   Y   L   R   N   V   A   L   V   S   G   D   T   E   N   A   K   G 1683            1692            1701            1710            1719            1728
CAG GGG GAG CAG GGC TCA ACT GGA GGA ACA AAT ATC AGC TCC ACC TCT GAG CCC
 Q   G   E   Q   G   S   T   G   G   T   N   I   S   S   T   S   E   P 1737            1746            1755            1764            1773            1782
AAG GAA GAA TGA GTC ACC CCA GAG CCC TAG AGG GTC AGA TGG GGG GAA CCC CAC
 K   E   E 1791            1800            1809            1818            1827            1836
CCT GCC CCA CCC ATC TGA ACA CTC ATT ACA CTA AAC ACC TCT TGG ATT TGG TGT 1845            1854            1863            1872            1881            1890
CCT CAT TGT CTA TCT AAT GTC TCA CCC GCA GTG TTT TAA GTG GAT CTT GGT GCC

1899
CTG GCC CAG G 3'
```

| | | |
|---|---|---|
| 1 | M G T T A R A A L V L T Y L A V A S A A | 1621777 |
| 1 | M G T V S R A A L I L A C L A L A S A A | GI 496120 |
| 21 | S E G G F T A T G Q R Q L R P E - - - - | 1621777 |
| 21 | S E G A F K A S D Q R E M T P E R L F Q | GI 496120 |
| 37 | H F Q E V G Y A A P P S P P L S R S L P | 1621777 |
| 41 | H L H E V G Y A A P P S L P Q T R R L R | GI 496120 |
| 57 | M D H P D S S Q H G P P - F E G Q S Q V | 1621777 |
| 61 | V D H S V T S L H D P P L F E E Q R E V | GI 496120 |
| 76 | Q P P P S Q E A T P L Q Q E K L L P A Q | 1621777 |
| 81 | Q P P S S P E D I P V Y E D W P T F L | GI 496120 |
| 96 | L P A E K E V G P P L P Q E A V P L Q K | 1621777 |
| 101 | N P N V D K A G P A V P Q E A I P L Q K | GI 496120 |
| 116 | E L P S L Q - - - - - - - - - - - H P | 1621777 |
| 121 | E Q P P P Q V H I E Q K E I D P P A Q P | GI 496120 |
| 124 | N E - - - Q K E G M P A P F G D Q S H P | 1621777 |
| 141 | Q E E I V Q K E V K P H T L A G Q L P P | GI 496120 |
| 141 | E P E S W N A A Q H C Q Q D R S Q G G W | 1621777 |
| 161 | E P R T W N P A R H C Q Q G R - R G V W | GI 496120 |
| 161 | G H R L D G F P P G R P S P D N L N Q I | 1621777 |
| 180 | G H R L D G F P P G R P S P D N L K Q I | GI 496120 |
| 181 | C L P N R Q H V V Y G P W N L P Q S S Y | 1621777 |
| 200 | C L P E R Q H V I Y G P W N L P Q T G Y | GI 496120 |
| 201 | S H L T R Q G E T L N F L E I G Y S R C | 1621777 |
| 220 | S H L S R Q G E T L N V L E T G Y S R C | GI 496120 |

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 448 amino acids
      (B) TYPE: amino acid
      (C) STRANDEDNESS: single
      (D) TOPOLOGY: linear (vii) IMMEDIATE SOURCE:
      (A) LIBRARY: CORNNOT01
      (B) CLONE: 45517

(xi) SEQUENCE DESCRIPTION: SEQ ID NO:1:

```
Met Pro Gly Ile Lys Arg Ile Leu Thr Val Thr Ile Leu Ala Leu Cys
 1               5                  10                  15

Leu Pro Ser Pro Gly Asn Ala Gln Ala Gln Cys Thr Asn Gly Phe Asp
            20                  25                  30

Leu Asp Arg Gln Ser Gly Gln Cys Leu Asp Ile Asp Glu Cys Arg Thr
        35                  40                  45
```

```
Ile Pro Glu Ala Cys Arg Gly Asp Met Met Cys Val Asn Gln Asn Gly
 50                  55                  60
Gly Tyr Leu Cys Ile Pro Arg Thr Asn Pro Val Tyr Arg Gly Pro Tyr
 65                  70                  75                  80
Ser Asn Pro Tyr Ser Thr Pro Tyr Ser Gly Pro Tyr Pro Ala Ala Ala
                 85                  90                  95
Pro Pro Leu Ser Ala Pro Asn Tyr Pro Thr Ile Ser Arg Pro Leu Ile
                100                 105                 110
Cys Arg Phe Gly Tyr Gln Met Asp Glu Ser Asn Gln Cys Val Asp Val
            115                 120                 125
Asp Glu Cys Ala Thr Asp Ser His Gln Cys Asn Pro Thr Gln Ile Cys
130                 135                 140
Ile Asn Thr Glu Gly Gly Tyr Thr Cys Ser Cys Thr Asp Gly Tyr Trp
145                 150                 155                 160
Leu Leu Glu Gly Gln Cys Leu Asp Ile Asp Glu Cys Arg Tyr Gly Tyr
                165                 170                 175
Cys Gln Gln Leu Cys Ala Asn Val Pro Gly Ser Tyr Ser Cys Thr Cys
            180                 185                 190
Asn Pro Gly Phe Thr Leu Asn Glu Asp Gly Arg Ser Cys Gln Asp Val
            195                 200                 205
Asn Glu Cys Ala Thr Glu Asn Pro Cys Val Gln Thr Cys Val Asn Thr
210                 215                 220
Tyr Gly Ser Phe Ile Cys Arg Cys Asp Pro Gly Tyr Glu Leu Glu Glu
225                 230                 235                 240
Asp Gly Val His Cys Ser Asp Met Asp Glu Cys Ser Phe Ser Glu Phe
                245                 250                 255
Leu Cys Gln His Glu Cys Val Asn Gln Pro Gly Thr Tyr Phe Cys Ser
            260                 265                 270
Cys Pro Pro Gly Tyr Ile Leu Leu Asp Asp Asn Arg Ser Cys Gln Asp
            275                 280                 285
Ile Asn Glu Cys Glu His Arg Asn His Thr Cys Asn Leu Gln Gln Thr
290                 295                 300
Cys Tyr Asn Leu Gln Gly Gly Phe Lys Cys Ile Asp Pro Ile Arg Cys
305                 310                 315                 320
Glu Glu Pro Tyr Leu Arg Ile Ser Asp Asn Arg Cys Met Cys Pro Ala
                325                 330                 335
Glu Asn Pro Gly Cys Arg Asp Gln Pro Phe Thr Ile Leu Tyr Arg Asp
            340                 345                 350
Met Asp Val Val Ser Gly Arg Ser Val Pro Ala Asp Ile Phe Gln Met
            355                 360                 365
Gln Ala Thr Thr Arg Tyr Pro Gly Ala Tyr Tyr Ile Phe Gln Ile Lys
370                 375                 380
Ser Gly Asn Glu Gly Arg Glu Phe Tyr Met Arg Gln Thr Gly Pro Ile
385                 390                 395                 400
Ser Ala Thr Leu Val Met Thr Arg Pro Ile Lys Gly Pro Arg Glu Ile
                405                 410                 415
Gln Leu Asp Leu Glu Met Ile Thr Val Asn Thr Val Ile Asn Phe Arg
            420                 425                 430
Gly Ser Ser Val Ile Arg Leu Arg Ile Tyr Val Ser Gln Tyr Pro Phe
            435                 440                 445
```

(2) INFORMATION FOR SEQ ID NO:2:

(i) SEQUENCE CHARACTERISTICS:
  (A) LENGTH: 2550 base pairs
  (B) TYPE: nucleic acid
  (C) STRANDEDNESS: single
  (D) TOPOLOGY: linear (vii) IMMEDIATE SOURCE:
  (A) LIBRARY: CORNNOT01
  (B) CLONE: 45517

(xi) SEQUENCE DESCRIPTION: SEQ ID NO:2:

```
CCAAGATTGT TGTGAGGAGT CTAGCCAGTT GGTGAGCGCT GTAATCTGAA CCAGCTGTGT      60
CCAGACTGAG GCCCCATTTG CATTATTTAA CATACTTAGA AAATGAAGTG TTCATTTTTA     120
ACATTCCTCC TCCAATTGGT TTAATGCTGA ATTACTGAAG AGGGCTAAGC AAAACCAGGT     180
GCTTGCGCTG AGGGCTCTGC AGTGGCTGGG AGGACCCCGG CGCTCTCCCC GTGTCCTCTC     240
CACGACTCGC TCGGCCCCTC TGGAATAAAA CACCCGCGAG CCCCGAGGGC CCAGAGGAGG     300
CCGACGTGCC CGAGCTCCTC CGGGGGTCCC GCCCGCGAGC TTTCTTCTCG CCTTCGCATC     360
TCCTCCTCGC GCGTCTTGGA CATGCCAGGA ATAAAAAGGA TACTCACTGT TACCATTCTG     420
GCTCTCTGTC TTCCAAGCCC TGGGAATGCA CAGGCACAGT GCACGAATGG CTTTGACCTG     480
GATCGCCAGT CAGGACAGTG TTTAGATATT GATGAATGCC GAACCATCCC CGAGGCCTGC     540
CGAGGAGACA TGATGTGTGT TAACCAAAAT GGCGGGTATT TATGCATTCC CCGGACAAAC     600
CCTGTGTATC GAGGGCCCTA CTCGAACCCC TACTCGACCC CCTACTCAGG TCCGTACCCA     660
GCAGCTGCCC CACCACTCTC AGCTCCAAAC TATCCCACGA TCTCCAGGCC TCTTATATGC     720
CGCTTTGGAT ACCAGATGGA TGAAAGCAAC CAATGTGTGG ATGTGGACGA GTGTGCAACA     780
GATTCCCACC AGTGCAACCC CACCCAGATC TGCATCAATA CTGAAGGCGG GTACACCTGC     840
TCCTGCACCG ACGGATATTG GCTTCTGGAA GGCCAGTGCT TAGACATTGA TGAATGTCGC     900
TATGGTTACT GCCAGCAGCT CTGTGCGAAT GTTCCTGGAT CCTATTCTTG TACATGCAAC     960
CCTGGTTTTA CCCTCAATGA GGATGGAAGG TCTTGCCAAG ATGTGAACGA GTGTGCCACC    1020
GAGAACCCCT GCGTGCAAAC CTGCGTCAAC ACCTACGGCT CTTTCATCTG CCGCTGTGAC    1080
CCAGGATATG AACTTGAGGA AGATGGCGTT CATTGCAGTG ATATGGACGA GTGCAGCTTC    1140
TCTGAGTTCC TCTGCCAACA TGAGTGTGTG AACCAGCCCG GCACATACTT CTGCTCCTGC    1200
CCTCCAGGCT ACATCCTGCT GGATGACAAC CGAAGCTGCC AAGACATCAA CGAATGTGAG    1260
CACAGGAACC ACACGTGCAA CCTGCAGCAG ACGTGCTACA ATTTACAAGG GGCTTCAAA    1320
TGCATCGACC CCATCCGCTG TGAGGAGCCT TATCTGAGGA TCAGTGATAA CCGCTGTATG    1380
TGTCCTGCTG AGAACCCTGG CTGCAGAGAC CAGCCCTTTA CCATCTTGTA CCGGGACATG    1440
GACGTGGTGT CAGGACGCTC CGTTCCCGCT GACATCTTCC AAATGCAAGC CACGACCCGC    1500
TACCCTGGGG CCTATTACAT TTTCCAGATC AAATCTGGGA ATGAGGGCAG AGAATTTTAC    1560
ATGCGGCAAA CGGGCCCCAT CAGTGCCACC CTGGTGATGA CACGCCCCAT CAAAGGGCCC    1620
CGGGAAATCC AGCTGGACTT GGAAATGATC ACTGTCAACA CTGTCATCAA CTTCAGAGGC    1680
AGCTCCGTGA TCCGACTGCG GATATATGTG TCGCAGTACC CATTCTGAGC CTCGGGCTGG    1740
AGCCTCCGAC GCTGCCTCTC ATTGGCACCA AGGGACAGGA GAAGAGAGGA AATAACAGAG    1800
AGAATGAGAG CGACACAGAC GTTAGGCATT TCCTGCTGAA CGTTTCCCCG AAGAGTCAGC    1860
CCCGACTTCC TGACTCTCAC CTGTACTATT GCAGACCTGT CACCCTGCAG GACTTGCCAC    1920
CCCCAGTTCC TATGACACAG TTATCAAAAA GTATTATCAT TGCTCCCCTG ATAGAAGATT    1980
GTTGGTGAAT TTTCAAGGCC TTCAGTTTAT TTCCACTATT TTCAAAGAAA ATAGATTAGG    2040
```

-continued

```
TTTGCGGGGG TCTGAGTCTA TGTTCAAAGA CTGTGAACAG CTTGCTGTCA CTTCTTCACC      2100

TCTTCCACTC CTTCTCTCAC TGTGTTACTG CTTTGCAAAG ACCCGGGAGC TGGCGGGGAA      2160

CCCTGGGAGT AGCTAGTTTG CTTTTTGCGT ACACAGAGAA GGCTATGTAA ACAAACCACA      2220

GCAGGATCGA AGGGTTTTTA GAGAATGTGT TTCAAAACCA TGCCTGGTAT TTTCAACCAT      2280

AAAAGAAGTT TCAGTTGTCC TTAAATTTGT ATAACGGTTT AATTCTGTCT TGTTCATTTT      2340

GAGTATTTTT AAAAAATATG TCGTAGAATT CCTTCGAAAG GCCTTCAGAC ACATGCTATG      2400

TTCTGTCTTC CCAAACCCAG TCTCCTCTCC ATTTTAGCCC AGTGTTTTCT TTGAGGACCC      2460

CTTAATCTTG CTTTCTTTAG AATTTTTACC CAATTGGATT GGAATGCAGA GGTCTCCAAA      2520

CTGATTAAAT ATTTGAAGAG AAAAAAAAAA                                       2550
```

(2) INFORMATION FOR SEQ ID NO:3:

(i) SEQUENCE CHARACTERISTICS:
        (A) LENGTH: 540 amino acids
        (B) TYPE: amino acid
        (C) STRANDEDNESS: single
        (D) TOPOLOGY: linear (vii) IMMEDIATE SOURCE:
        (A) LIBRARY: BRAITUT13
        (B) CLONE: 1621777

(xi) SEQUENCE DESCRIPTION: SEQ ID NO:3:

```
Met Gly Thr Thr Ala Arg Ala Ala Leu Val Leu Thr Tyr Leu Ala Val
  1               5                  10                  15

Ala Ser Ala Ala Ser Glu Gly Gly Phe Thr Ala Thr Gly Gln Arg Gln
                 20                  25                  30

Leu Arg Pro Glu His Phe Gln Glu Val Gly Tyr Ala Ala Pro Pro Ser
             35                  40                  45

Pro Pro Leu Ser Arg Ser Leu Pro Met Asp His Pro Asp Ser Ser Gln
     50                  55                  60

His Gly Pro Pro Phe Glu Gly Gln Ser Gln Val Gln Pro Pro Ser
 65                  70                  75                  80

Gln Glu Ala Thr Pro Leu Gln Gln Glu Lys Leu Leu Pro Ala Gln Leu
                 85                  90                  95

Pro Ala Glu Lys Glu Val Gly Pro Pro Leu Pro Gln Glu Ala Val Pro
            100                 105                 110

Leu Gln Lys Glu Leu Pro Ser Leu Gln His Pro Asn Glu Gln Lys Glu
            115                 120                 125

Gly Met Pro Ala Pro Phe Gly Asp Gln Ser His Pro Glu Pro Glu Ser
        130                 135                 140

Trp Asn Ala Ala Gln His Cys Gln Gln Asp Arg Ser Gln Gly Gly Trp
145                 150                 155                 160

Gly His Arg Leu Asp Gly Phe Pro Pro Gly Arg Pro Ser Pro Asp Asn
                165                 170                 175

Leu Asn Gln Ile Cys Leu Pro Arg Gln His Val Val Tyr Gly Pro
            180                 185                 190

Trp Asn Leu Pro Gln Ser Ser Tyr Ser His Leu Thr Arg Gln Gly Glu
            195                 200                 205

Thr Leu Asn Phe Leu Glu Ile Gly Tyr Ser Arg Cys Cys His Cys Arg
        210                 215                 220

Ser His Thr Asn Arg Leu Glu Cys Ala Lys Leu Val Trp Glu Glu Ala
225                 230                 235                 240
```

```
Met Ser Arg Phe Cys Glu Ala Glu Phe Ser Val Lys Thr Arg Pro His
            245                 250                 255

Trp Cys Cys Thr Arg Gln Gly Glu Ala Arg Phe Ser Cys Phe Gln Glu
            260                 265                 270

Glu Ala Pro Gln Pro His Tyr Gln Leu Arg Ala Cys Pro Ser His Gln
            275                 280                 285

Pro Asp Ile Ser Ser Gly Leu Glu Leu Pro Phe Pro Pro Gly Val Pro
            290                 295                 300

Thr Leu Asp Asn Ile Lys Asn Ile Cys His Leu Arg Arg Phe Arg Ser
305                 310                 315                 320

Val Pro Arg Asn Leu Pro Ala Thr Asp Pro Leu Gln Arg Glu Leu Leu
            325                 330                 335

Ala Leu Ile Gln Leu Glu Arg Glu Phe Gln Arg Cys Cys Arg Gln Gly
            340                 345                 350

Asn Asn His Thr Cys Thr Trp Lys Ala Trp Glu Asp Thr Leu Asp Lys
            355                 360                 365

Tyr Cys Asp Arg Glu Tyr Ala Val Lys Thr His His Leu Cys Cys
            370                 375                 380

Arg His Pro Pro Ser Pro Thr Arg Asp Glu Cys Phe Ala Arg Arg Ala
385                 390                 395                 400

Pro Tyr Pro Asn Tyr Asp Arg Asp Ile Leu Thr Ile Asp Ile Gly Arg
            405                 410                 415

Val Thr Pro Asn Leu Met Gly His Leu Cys Gly Asn Gln Arg Val Leu
            420                 425                 430

Thr Lys His Lys His Ile Pro Gly Leu Ile His Asn Met Thr Ala Arg
            435                 440                 445

Cys Cys Asp Leu Pro Phe Pro Glu Gln Ala Cys Cys Ala Glu Glu Glu
            450                 455                 460

Lys Leu Thr Phe Ile Asn Asp Leu Cys Gly Pro Arg Arg Asn Ile Trp
465                 470                 475                 480

Arg Asp Pro Ala Leu Cys Cys Tyr Leu Ser Pro Gly Asp Glu Gln Val
            485                 490                 495

Asn Cys Phe Asn Ile Asn Tyr Leu Arg Asn Val Ala Leu Val Ser Gly
            500                 505                 510

Asp Thr Glu Asn Ala Lys Gly Gln Gly Glu Gln Gly Ser Thr Gly Gly
            515                 520                 525

Thr Asn Ile Ser Ser Thr Ser Glu Pro Lys Glu Glu
            530                 535                 540

(2) INFORMATION FOR SEQ ID NO:4:

(i) SEQUENCE CHARACTERISTICS:
        (A) LENGTH: 1899 base pairs
        (B) TYPE: nucleic acid
        (C) STRANDEDNESS: single
        (D) TOPOLOGY: linear (vii) IMMEDIATE SOURCE:
        (A) LIBRARY: BRAITUT13
        (B) CLONE: 162177

(xi) SEQUENCE DESCRIPTION: SEQ ID NO:4:

TGGGTGCAAG CTCACAACCG TAACAGCCAC CAGACAAGCT TCAGTGGCCG GCCCTTCACA        60

TCCAGACTTG CCTGAGAGGA CCCACCTCTG AGTGTCCAGT GGTCAGTTGC CCCAGGATGG       120

GGACCACAGC CAGAGCAGCC TTGGTCTTGA CCTATTTGGC TGTTGCTTCT GCTGCCTCTG       180

AGGGAGGCTT CACGGCTACA GGACAGAGGC AGCTGAGGCC AGAGCACTTT CAAGAAGTTG       240
```

```
GCTACGCAGC TCCCCCCTCC CCACCCCTAT CCCGAAGCCT CCCCATGGAT CACCCTGACT      300

CCTCTCAGCA TGGCCCTCCC TTTGAGGGAC AGAGTCAAGT GCAGCCCCCT CCCTCTCAGG      360

AGGCCACCCC TCTCCAACAG GAAAAGCTGC TACCTGCCCA ACTCCCTGCT GAAAAGGAAG      420

TGGGTCCCCC TCTCCCTCAG GAAGCTGTCC CCCTCCAAAA AGAGCTGCCC TCTCTCCAGC      480

ACCCCAATGA ACAGAAGGAA GGAATGCCAG CTCCATTTGG GGACCAGAGC CATCCAGAAC      540

CTGAGTCCTG GAATCAGCC CAGCACTGCC AACAGGACCG GTCCCAAGGG GGCTGGGGCC       600

ACCGGCTGGA TGGCTTCCCC CCTGGGCGGC CTTCTCCAGA CAATCTGAAC CAAATCTGCC      660

TTCCTAACCG TCAGCATGTG GTATATGGTC CCTGGAACCT ACCACAGTCC AGCTACTCCC      720

ACCTCACTCG CCAGGGTGAG ACCCTCAATT TCCTGGAGAT TGGATATTCC CGCTGCTGCC      780

ACTGCCGCAG CCACACAAAC CGCCTAGAGT GTGCCAAACT TGTGTGGGAG GAAGCAATGA      840

GCCGATTCTG TGAGGCCGAG TTCTCGGTCA AGACCCGACC CCACTGGTGC TGCACGCGGC      900

AGGGGGAGGC TCGGTTCTCC TGCTTCCAGG AGGAAGCTCC CCAGCCACAC TACCAGCTCC      960

GGGCCTGCCC CAGCCATCAG CCTGATATTT CCTCGGGTCT TGAGCTGCCT TTCCCTCCTG     1020

GGGTGCCCAC ATTGGACAAT ATCAAGAACA TCTGCCACCT GAGGCGCTTC CGCTCTGTGC     1080

CACGCAACCT GCCAGCTACT GACCCCCTAC AAAGGGAGCT GCTGGCACTG ATCCAGCTGG     1140

AGAGGGAGTT CCAGCGCTGC TGCCGCCAGG GGAACAATCA CACCTGTACA TGGAAGGCCT     1200

GGGAGGATAC CCTTGACAAA TACTGTGACC GGGAGTATGC TGTGAAGACC ACCACCACT      1260

TGTGTTGCCG CCACCCTCCC AGCCCTACTC GGGATGAGTG CTTTGCCCGT CGGGCTCCTT     1320

ACCCCAACTA TGACCGGGAC ATCTTGACCA TTGACATCGG TCGAGTCACC CCCAACCTCA     1380

TGGGCCACCT CTGTGGAAAC CAAAGAGTTC TCACCAAGCA TAAACATATT CCTGGGCTGA     1440

TCCACAACAT GACTGCCCGC TGCTGTGACC TGCCATTTCC AGAACAGGCC TGCTGTGCAG     1500

AGGAGGAGAA ATTAACCTTC ATCAATGATC TGTGTGGTCC CCGACGTAAC ATCTGGCGAG     1560

ACCCTGCCCT CTGCTGTTAC CTGAGTCCTG GGGATGAACA GGTCAACTGC TTCAACATCA     1620

ATTATCTGAG GAACGTGGCT CTAGTGTCTG GAGACACTGA GAACGCCAAG GGCCAGGGGG     1680

AGCAGGGCTC AACTGGAGGA ACAAATATCA GCTCCACCTC TGAGCCCAAG GAAGAATGAG     1740

TCACCCCAGA GCCCTAGAGG GTCAGATGGG GGGAACCCCA CCCTGCCCCA CCCATCTGAA     1800

CACTCATTAC ACTAAACACC TCTTGGATTT GGTGTCCTCA TTGTCTATCT AATGTCTCAC     1860

CCGCAGTGTT TTAAGTGGAT CTTGGTGCCC TGGCCCAGG                            1899
```

(2) INFORMATION FOR SEQ ID NO:5:

(i) SEQUENCE CHARACTERISTICS:
        (A) LENGTH: 387 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 458228

(xi) SEQUENCE DESCRIPTION: SEQ ID NO:5:

```
Met Ala Thr Ser Gly Val Leu Pro Gly Gly Phe Val Ala Ser Ala
 1               5                  10                  15

Ala Ala Val Ala Gly Pro Glu Met Gln Thr Gly Arg Asn Asn Phe Val
                20                  25                  30

Ile Arg Arg Asn Pro Ala Asp Pro Gln Arg Ile Pro Ser Asn Pro Ser
```

-continued

```
                35                  40                  45
His Arg Ile Gln Cys Ala Ala Gly Tyr Glu Gln Ser Glu His Asn Val
         50                  55                  60

Cys Gln Asp Ile Asp Glu Cys Thr Ala Gly Thr His Asn Cys Arg Ala
 65                  70                  75                  80

Asp Gln Val Cys Ile Asn Leu Arg Gly Ser Phe Ala Cys Gln Cys Pro
                 85                  90                  95

Pro Gly Tyr Gln Lys Arg Gly Glu Gln Cys Val Asp Ile Asp Glu Cys
                100                 105                 110

Thr Ile Pro Pro Tyr Cys His Gln Arg Cys Val Asn Thr Pro Gly Ser
                115                 120                 125

Phe Tyr Cys Gln Cys Ser Pro Gly Phe Gln Leu Ala Ala Asn Asn Tyr
            130                 135                 140

Thr Cys Val Asp Ile Asn Glu Cys Asp Ala Ser Asn Gln Cys Ala Gln
145                 150                 155                 160

Gln Cys Tyr Asn Ile Leu Gly Ser Phe Ile Cys Gln Cys Asn Gln Gly
                165                 170                 175

Tyr Glu Leu Ser Ser Asp Arg Leu Asn Cys Glu Asp Ile Asp Glu Cys
            180                 185                 190

Arg Thr Ser Ser Tyr Leu Cys Gln Tyr Gln Cys Val Asn Glu Pro Gly
        195                 200                 205

Lys Phe Ser Cys Met Cys Pro Gln Gly Tyr Gln Val Val Arg Ser Arg
    210                 215                 220

Thr Cys Gln Asp Ile Asn Glu Cys Glu Thr Thr Asn Glu Cys Arg Glu
225                 230                 235                 240

Asp Glu Met Cys Trp Asn Tyr His Gly Gly Phe Arg Cys Tyr Pro Arg
                245                 250                 255

Asn Pro Cys Gln Asp Pro Tyr Ile Leu Thr Pro Glu Asn Arg Cys Val
            260                 265                 270

Cys Pro Val Ser Asn Ala Met Cys Arg Glu Leu Pro Gln Ser Ile Val
        275                 280                 285

Tyr Lys Tyr Met Ser Ile Arg Ser Asp Arg Ser Val Pro Ser Asp Ile
    290                 295                 300

Phe Gln Ile Gln Ala Thr Thr Ile Tyr Ala Asn Thr Ile Asn Thr Phe
305                 310                 315                 320

Arg Ile Lys Ser Gly Asn Glu Asn Gly Glu Phe Tyr Leu Arg Gln Thr
                325                 330                 335

Ser Pro Val Ser Ala Met Leu Val Leu Val Lys Ser Leu Ser Gly Pro
            340                 345                 350

Arg Glu His Ile Val Asp Leu Glu Met Leu Thr Val Ser Ser Ile Gly
        355                 360                 365

Thr Phe Arg Thr Ser Ser Val Leu Arg Leu Thr Ile Ile Val Gly Pro
    370                 375                 380

Phe Ser Phe
385
```

(2) INFORMATION FOR SEQ ID NO:6:

(i) SEQUENCE CHARACTERISTICS:
    (A) LENGTH: 559 amino acids
    (B) TYPE: amino acid
    (C) STRANDEDNESS: single
    (D) TOPOLOGY: linear (vii) IMMEDIATE SOURCE:
    (A) LIBRARY: GenBank (B) CLONE: 496120

(xi) SEQUENCE DESCRIPTION: SEQ ID NO:6:

```
Met Gly Thr Val Ser Arg Ala Ala Leu Ile Leu Ala Cys Leu Ala Leu
 1               5                  10                  15

Ala Ser Ala Ser Glu Gly Ala Phe Lys Ala Ser Asp Gln Arg Glu
            20                  25                  30

Met Thr Pro Glu Arg Leu Phe Gln His Leu His Glu Val Gly Tyr Ala
            35                  40                  45

Ala Pro Pro Ser Leu Pro Gln Thr Arg Arg Leu Arg Val Asp His Ser
    50                  55                  60

Val Thr Ser Leu His Asp Pro Pro Leu Phe Glu Glu Gln Arg Glu Val
 65                  70                  75                  80

Gln Pro Pro Ser Ser Pro Glu Asp Ile Pro Val Tyr Glu Glu Asp Trp
                85                  90                  95

Pro Thr Phe Leu Asn Pro Asn Val Asp Lys Ala Gly Pro Ala Val Pro
                100                 105                 110

Gln Glu Ala Ile Pro Leu Gln Lys Glu Gln Pro Pro Gln Val His
            115                 120                 125

Ile Glu Gln Lys Glu Ile Asp Pro Pro Ala Gln Pro Gln Glu Ile
130                 135                 140

Val Gln Lys Glu Val Lys Pro His Thr Leu Ala Gly Gln Leu Pro Pro
145                 150                 155                 160

Glu Pro Arg Thr Trp Asn Pro Ala Arg His Cys Gln Gln Gly Arg Arg
                165                 170                 175

Gly Val Trp Gly His Arg Leu Asp Gly Phe Pro Pro Gly Arg Pro Ser
                180                 185                 190

Pro Asp Asn Leu Lys Gln Ile Cys Leu Pro Glu Arg Gln His Val Ile
        195                 200                 205

Tyr Gly Pro Trp Asn Leu Pro Gln Thr Gly Tyr Ser His Leu Ser Arg
    210                 215                 220

Gln Gly Glu Thr Leu Asn Val Leu Glu Thr Gly Tyr Ser Arg Cys Cys
225                 230                 235                 240

Pro Cys Arg Ser Asp Thr Asn Arg Leu Asp Cys Leu Lys Leu Val Trp
                245                 250                 255

Glu Asp Ala Met Thr Gln Phe Cys Glu Ala Glu Phe Ser Val Lys Thr
                260                 265                 270

Arg Pro His Leu Cys Cys Arg Leu Arg Gly Glu Arg Phe Ser Cys
                275                 280                 285

Phe Gln Lys Glu Ala Pro Arg Pro Asp Tyr Leu Leu Arg Pro Cys Pro
    290                 295                 300

Val His Gln Asn Gly Met Ser Ser Gly Pro Gln Leu Pro Phe Pro Pro
305                 310                 315                 320

Gly Leu Pro Thr Pro Asp Asn Val Lys Asn Ile Cys Leu Leu Arg Arg
                325                 330                 335

Phe Arg Ala Val Pro Arg Asn Leu Pro Ala Thr Asp Ala Ile Gln Arg
                340                 345                 350

Gln Leu Gln Ala Leu Thr Arg Leu Glu Thr Glu Phe Gln Arg Cys Cys
            355                 360                 365

Arg Gln Gly His Asn His Thr Cys Thr Trp Lys Ala Trp Glu Gly Thr
    370                 375                 380

Leu Asp Gly Tyr Cys Glu Arg Glu Leu Ala Ile Lys Thr His Pro His
385                 390                 395                 400
```

```
                      -continued

Ser Cys Cys His Tyr Pro Pro Ser Pro Ala Arg Asp Glu Cys Phe Ala
            405                 410                 415

His Leu Ala Pro Tyr Pro Asn Tyr Asp Arg Asp Ile Leu Thr Leu Asp
            420                 425                 430

Leu Ser Arg Val Thr Pro Asn Leu Met Gly Gln Leu Cys Gly Ser Gly
        435                 440                 445

Arg Val Leu Ser Lys His Lys Gln Ile Pro Gly Leu Ile Gln Asn Met
    450                 455                 460

Thr Val Arg Cys Cys Glu Leu Pro Tyr Pro Glu Gln Ala Cys Cys Gly
465                 470                 475                 480

Glu Glu Glu Lys Leu Ala Phe Ile Glu Asn Leu Cys Gly Pro Arg Arg
            485                 490                 495

Asn Ser Trp Lys Asp Pro Ala Leu Cys Cys Asp Leu Ser Pro Glu Asp
            500                 505                 510

Lys Gln Ile Asn Cys Phe Asn Thr Asn Tyr Leu Arg Asn Val Ala Leu
        515                 520                 525

Val Ala Gly Asp Thr Gly Asn Ala Thr Gly Leu Gly Glu Gln Gly Pro
    530                 535                 540

Thr Arg Gly Thr Asp Ala Asn Pro Ala Pro Gly Ser Lys Glu Glu
545                 550                 555
```

HUMAN EXTRACELLULAR MATRIX PROTEINS

This application is a divisional of Ser. No. 08/884,072, filed Jun. 27, 1997 now U.S. Pat. No. 5,872,234.

FIELD OF THE INVENTION

This invention relates to nucleic acid and amino acid sequences of human extracellular matrix proteins and to the use of these sequences in the diagnosis, prevention, and treatment of cancer and immune disorders.

BACKGROUND OF THE INVENTION

Many eukaryotic cells are enveloped by an extracellular matrix of proteins that provide structural support, cell and tissue identity, and autocrine, paracrine and juxtacrine properties for the cell within its environment (McGowan, S. E. (1992) FASEB J. 6:2895–2904). The diverse biochemistry of extracellular matrix proteins (ECMP) is indicative of the many, often overlapping, roles that are attributed to each distinct molecule (cf. Grant, D. S. and Kleinman, H. K. (1997) E.X.S. 79:317–333). Whilst a great number of ECMPs have been isolated, it still remains unclear how the majority interact with other ECMPs or with molecules residing within the cell membrane. Many ECMPs have been associated with tissue growth and cell proliferation, others with tissue or cell differentiation, and yet others with cell death (cf. Taipale, J. and Keski-Oja, J. (1997) FASEB J. 11:51–59; Eleftheriou, C. S. et al. (1991) Mutat. Res. 256:127–138).

For example, the process of embryonic bone formation involves the creation of an extracellular matrix that mineralizes during the course of tissue maturation. During the life of an individual, this matrix is subject to constant remodeling, through the combined actions of osteoblasts (which form mineralized bone) and osteoclasts (which resorb bone). The balance of ECMP composition, and the resulting bone structure, may be perturbed by biochemical changes that result from congenital, epigenetic, or infectious diseases (Francomano, C. A. et al. (1996) Curr. Opin. Genet. Dev. 6:301–308).

ECMPs also act as important mediators and regulators during the inflammatory response. Leukocytes are primed for inflammatory mediator and cytokine production by binding to ECMPs during extravasation (Pakianathan, D. R. (1995) J. Leukoc. Biol. 57:699–702). Deposition of ECMPs is also triggered by inflammation in response to lung injury (Roman, J. (1996) Immunol. Res. 15:163–178). Although the function of newly deposited matrices in injured lungs is unknown, their ability to affect the migration, proliferation, differentiation, and activation state of cells in vitro suggested an important role in the initiation and maintenance of the inflammatory response in vivo (Roman, supra)

Some examples of recently identified ECMPs which regulate cellular and tissue differentiation are S1-5 and Ecml. S1-5 mRNA is overexpressed both in senescent human fibroblasts established from a subject with Werner syndrome of premature ageing and in growth-arrested normal human fibroblasts (Lecka-Czernik, B. et al. (1995) Mol. Cell. Biol. 15:120–128). The MRNA encodes a 387 amino acid residue protein containing five epidermal growth factor (EGF)-like domains. These domains matched the EGF tandem repeat consensus within several known extracellular proteins that promote cell growth, development, and cell signaling. The EGF tandem repeat is characterized by a regular distribution of single cysteines. As occurs with other members of the EGF-like family, the S1-5 gene product may represent a negative and/or positive factor whose ultimate activity is modulated by the cell environment (Lecka-Czernik, supra).

Murine Ecm1 encodes a 559 residue protein that has been localized to one genetic locus associated with developmental disorders of the skin (Bhalerao, J. et al. (1995) J. Biol. Chem. 270:16385–16394). During embryonic development, the gene is predominantly expressed in the form of splice variants in skin or cartilage tissue. Expression of the Ecm1 gene also peaks during the late, pre-confluence phase of the murine osteogenic cell line, MN7, which proliferates and differentiates in vitro forming a mineralized matrix (Bhalerao, supra). The murine Ecm1 gene has been localized by genetic mapping to mouse chromosome 3, a region homologous to that of human chromosome 1q21 (Bhalerao, supra). The molecular structure of the predicted protein is characterized by a pair of domains which share internal homology, and by a regular distribution of single cysteines and cysteine doublets. The latter arrangement was predicted to generate characteristic 'double-loop' proteins in the serum albumin family of proteins (Soltysik-Espanola, M. et al. (1994) Dev. Biol. 165:73–85). These double-loop structures are involved in important ligand-binding functions (Kragh-Hansen, U. (1990) Danish Med. Bull. 37:57–84).

The discovery of new human extracellular matrix proteins and the polynucleotides encoding them satisfies a need in the art by providing new compositions which are useful in the diagnosis, prevention and treatment of cancer and immune disorders.

SUMMARY OF THE INVENTION

The invention features substantially purified human extracellular matrix proteins, collectively referred to as ECMP and individually as ECMP-1, and ECMP-2, having the amino acid sequence shown in SEQ ID NO:1, or SEQ ID NO:3, respectively, or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO.2 or variants thereof. In addition, the invention provides a polynucleotide sequence which hybridizes under stringent conditions to the polynucleotide sequence of SEQ ID NO:2. In another aspect the invention provides a composition comprising an isolated and purified polynucleotide sequence comprising the complement of SEQ ID NO:2, or fragments or variants thereof. The invention also provides a polynucleotide sequence comprising the complement of SEQ ID NO:2.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding ECMP-1 under conditions suitable for the expression of the polypeptide; and b) recovering the polypeptide from the host cell culture.

The invention also provides a pharmaceutical composition comprising a substantially purified ECMP-1 having the amino acid sequence of SEQ ID NO:1 in conjunction with a suitable pharmaceutical carrier.

The invention also provides a purified antagonist which decreases the activity of a polypeptide of SEQ ID NO:1. In one aspect the invention provides a purified antibody which binds to a polypeptide comprising at least a fragment of the amino acid sequence of SEQ ID NO:1.

Still further, the invention provides a purified agonist which modulates the activity of the polypeptide of SEQ ID NO:1.

The invention also provides a method for treating or preventing cancer comprising administering to a subject in need of such treatment an effective amount of a purified antagonist of ECMP-1.

The invention also provides a method for treating or preventing an immune disorder comprising administering to a subject in need of such treatment an effective amount of a purified antagonist of ECMP-1.

The invention also provides a method for detecting a polynucleotide which encodes ECMP-1 in a biological sample comprising the steps of: a) hybridizing a polynucleotide sequence complementary to the polynucleotide sequence encoding ECMP-1 (SEQ ID NO:1) to nucleic acid material of a biological sample, thereby forming a hybridization complex; and b) detecting the hybridization complex, wherein the presence of the complex correlates with the presence of a polynucleotide encoding ECMP-1 in the biological sample. In a preferred embodiment, prior to hybridization, the nucleic acid material of the biological sample is amplified by the polymerase chain reaction.

The invention further provides an isolated and substantially purified polynucleotide sequence encoding the polypeptide comprising the amino acid sequence of SEQ ID NO:3 or fragments thereof and a composition comprising said polynucleotide sequence. The invention also provides a polynucleotide sequence which hybridizes under stringent conditions to the polynucleotide sequence encoding the amino acid sequence SEQ ID NO:3, or fragments of said polynucleotide sequence. The invention further provides a polynucleotide sequence comprising the complement of the polynucleotide sequence encoding the amino acid sequence of SEQ ID NO:3, or fragments or variants of said polynucleotide sequence.

The invention also provides an isolated and purified sequence comprising SEQ ID NO.4 or variants thereof. In addition, the invention provides a polynucleotide sequence which hybridizes under stringent conditions to the polynucleotide sequence of SEQ ID NO:4. In another aspect the invention provides a composition comprising an isolated and purified polynucleotide sequence comprising the complement of SEQ ID NO:4, or fragments or variants thereof. The invention also provides a polynucleotide sequence comprising the complement of SEQ ID NO:4.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:3 or a fragment thereof, the method comprising the steps of: a) culturing the host cell containing an expression vector containing at least a fragment of the polynucleotide sequence encoding ECMP-2 under conditions suitable for the expression of the polypeptide; and b) recovering the polypeptide from the host cell culture.

The invention also provides a pharmaceutical composition comprising a substantially purified ECMP-2 having the amino acid sequence of SEQ ID NO:3 in conjunction with a suitable pharmaceutical carrier.

The invention also provides a purified antagonist which decreases the activity of a polypeptide of SEQ ID NO:3. In one aspect the invention provides a purified antibody which binds to a polypeptide comprising at least a fragment of the amino acid sequence of SEQ ID NO:3.

Still further, the invention provides a purified agonist which modulates the activity of the polypeptide of SEQ ID NO:3.

The invention also provides a method for treating or preventing cancer comprising administering to a subject in need of such treatment an effective amount of a purified antagonist of ECMP-2.

The invention also provides a method for treating or preventing an immune disorder comprising administering to a subject in need of such treatment an effective amount of a purified antagonist of ECMP-2.

The invention also provides a method for detecting a polynucleotide which encodes ECMP-2 in a biological sample comprising the steps of: a) hybridizing a polynucleotide sequence complementary to the polynucleotide sequence encoding ECMP-2 (SEQ ID NO:3) to nucleic acid material of a biological sample, thereby forming a hybridization complex; and b) detecting the hybridization complex, wherein the presence of the complex correlates with the presence of a polynucleotide encoding ECMP-2 in the biological sample. In a preferred embodiment, the nucleic acid material of the biological sample is amplified by the polymerase chain reaction prior to hybridization.

BRIEF DESCRIPTION OF THE FIGURES

FIGS. 1A, 1B, 1C, 1D, 1E, 1F, and 1G show the amino acid sequence (SEQ ID NO:1) and nucleic acid sequence (SEQ ID NO:2) of ECMP-1. The alignment was produced using MACDNASIS PRO software (Hitachi Software Engineering, S. San Francisco, Calif.).

FIGS. 2A, 2B, 2C, 2D, and 2E show the amino acid sequence (SEQ ID NO:3) and nucleic acid sequence (SEQ ID NO:4) of ECMP-2. The alignment was produced using MACDNASIS PRO software.

FIGS. 3A, and 3B show the amino acid sequence alignments between ECMP-1 (SEQ ID NO:1) and human S1-5 gene product (GI 458228; SEQ ID NO:5), produced using the multisequence alignment program of LASERGENE software (DNASTAR, Madison Wis.).

FIGS. 4A, 4B, and 4C show the amino acid sequence alignments between ECMP-2 (SEQ ID NO:3), and murine secreted protein encoded by Ecm1 gene (GI 496120; SEQ ID NO:6), produced using the multisequence alignment program of LASERGENE software.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

ECMP refers to the amino acid sequences of substantially purified ECMP obtained from any species, particularly mammalian, including bovine, ovine, porcine, murine, equine, and preferably human, from any source whether natural, synthetic, semi-synthetic, or recombinant.

"Agonist" refers to a molecule which, when bound to ECMP, increases or prolongs the duration of the effect of ECMP. Agonists may include proteins, nucleic acids, carbohydrates, or any other molecules which bind to and modulate the effect of ECMP.

An "allele" or "allelic sequence" is an alternative form of the gene encoding ECMP. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding ECMP include those with deletions, insertions, or substitutions of different nucleotides resulting in a polynucleotide that encodes the same or a functionally equivalent ECMP. Included within this definition are polymorphisms which may or may not be readily detectable using a particular oligonucleotide probe of the polynucleotide encoding ECMP, and improper or unexpected hybridization to alleles, with a locus other than the normal chromosomal locus for the polynucleotide sequence encoding ECMP. The encoded protein may also be "altered" and contain deletions, insertions, or substitutions of amino acid residues which produce a silent change and result in a functionally equivalent ECMP. Deliberate amino acid substitutions may be made on the basis of similarity in polarity, charge, solubility, hydrophobicity, hydrophilicity, and/or the amphipathic nature of the residues as long as the biological or immunological activity of ECMP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" refers to an oligopeptide, peptide, polypeptide, or protein sequence, and fragment thereof, and to naturally occurring or synthetic molecules. Fragments of ECMP are preferably about 5 to about 15 amino acids in length and retain the biological activity or the immunological activity of ECMP. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

"Antagonist" refers to a molecule which, when bound to ECMP, decreases the amount or the duration of the effect of the biological or immunological activity of ECMP. Antagonists may include proteins, nucleic acids, carbohydrates, or any other molecules which decrease the effect of ECMP.

"Antibody" refers to intact molecules as well as fragments thereof, such as Fab, F(ab')$_2$, and Fv, which are capable of binding the epitopic determinant. Antibodies that bind ECMP polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

"Antigenic determinant" refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

"Antisense" refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

"Biologically active" refers to a protein having structural, regulatory, or biochemical functions of a naturally occurring molecule. Likewise, "immunologically active" refers to the capability of the natural, recombinant, or synthetic ECMP, or any oligopeptide thereof, to induce a specific immune response in appropriate animals or cells and to bind with specific antibodies.

"Complementary" or "complementarity" refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" refers broadly to any composition containing the given polynucleotide sequence. The composition may comprise a dry formulation or an aqueous solution. Compositions comprising polynucleotide sequences encoding ECMP (SEQ ID NO:1, SEQ ID NO:3) or fragments thereof (e.g., SEQ ID NO:2, or SEQ ID NO:4 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus" refers to a nucleic acid sequence which has been resequenced to resolve uncalled bases, has been extended using XL-PCR kit (PE Biosystems, Foster City, Calif.) in the 5' and/or the 3' direction and resequenced, or has been assembled from the overlapping sequences of more than one Incyte Clone using a computer program for fragment assembly (e.g., GELVIEW fragment assembly system, Genetics Computer Group, Madison, Wis.). Some sequences have been both extended and assembled to produce the consensus sequence.

The phrase "correlates with expression of a polynucleotide" indicates that the detection of the presence of ribonucleic acid that is similar to SEQ ID NO:2, or SEQ ID NO:4 by northern analysis is indicative of the presence of mRNA encoding ECMP in a sample and thereby correlates with expression of the transcript from the polynucleotide encoding the protein.

"Deletion" refers to a change in the amino acid or nucleotide sequence and results in the absence of one or more amino acid residues or nucleotides.

"Derivative" refers to the chemical modification of a nucleic acid encoding or complementary to ECMP or the encoded ECMP. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

"Homology" refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes are linear microchromosomes which may contain DNA sequences of 10K to 10M in size and contain all of the elements required for stable mitotic chromosome segregation and maintenance (Harrington, J. J. et al. (1997) Nat Genet. 15:345–355).

"Humanized antibody" refers to antibody molecules in which amino acids have been replaced in the non-antigen binding regions in order to more closely resemble a human antibody, while still retaining the original binding ability.

"Hybridization" refers to any process by which a strand of nucleic acid binds with a complementary strand through base pairing. "Hybridization complex" refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition" refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

"Modulate" refers to a change in the activity of ECMP. For example, modulation may cause an increase or a decrease in protein activity, binding characteristics, or any other biological, functional or immunological properties of ECMP.

"Nucleic acid sequence" refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

"Oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or hybridization assays and is substantially equivalent to the terms "amplimers","primers", "oligomers", and "probes", as commonly defined in the art.

"Peptide nucleic acid", PNA, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

"Portion" with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1, SEQ ID NO:3," encompasses the full-length ECMP and fragments thereof.

"Sample" is used in its broadest sense. A biological sample suspected of containing nucleic acid encoding ECMP, or fragments thereof, or ECMP itself may comprise a bodily fluid, extract from a cell, chromosome, organelle, or membrane isolated from a cell, a cell, genomic DNA, RNA, or cDNA (in solution or bound to a solid support, a tissue, a tissue print, and the like.

"Specific binding" or "specifically binding" refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

"Stringent conditions"or "stringency" refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

"Substantially purified" refers to nucleic or amino acid sequences that are removed from their natural environment, isolated or separated, and are at least 60% free, preferably 75% free, and most preferably 90% free from other components with which they are naturally associated.

A "substitution" refers to the replacement of one or more amino acids or nucleotides by different amino acids or nucleotides, respectively.

"Transformation" describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of ECMP refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

THE INVENTION

The invention is based on the discovery of a new human extracellular matrix proteins (collectively referred to as "ECMP" and individually, as ECMP-1 and ECMP-2), the polynucleotides encoding ECMP, and the use of these compositions for the diagnosis, prevention, or treatment of cancer and immune disorders.

Nucleic acids encoding the ECMP-1 of the present invention were first identified in Incyte Clone 45517 from the corneal fibroblast cDNA library (CORNNOT01) using a computer search for amino acid sequence alignments. A consensus sequence, SEQ ID NO:2, was derived from the following overlapping and/or extended nucleic acid sequences: Incyte Clones 45517 (CORNNOT01), 424333 (BLADNOT01), 1322651 (BLADNOT04), 198548 (KIDNNOT02), 944281 (ADRENOT03), and 953977 (SCORNON01).

In one embodiment, the invention encompasses a polypeptide comprising the amino acid sequence of SEQ ID NO:1, as shown in FIGS. 1A–1G. ECMP-1 is 449 amino acids in length and has five potential EGF-like tandem repeats between C-113 and C-341, four of which have the consensus repeat of $Cx\{11\text{-}12\}Cx\{5\}Cx\{4\text{-}6\}Cx\{3 \text{ or } 5\}Cx\{8\}CxC$ (where x represents any amino acid and {n} represents the number of residues). Within the EGF-like domain, there are four potential N-hydroxylation sites at N-146, N-183, N-223, and N-264; and two potential N-glycosylation sites at N-283, and N-296. The N-terminal 19 amino acids constitute a potential signal peptide sequence, and there is a potential cell attachment sequence, RGD, at R-54. There are eight potential casein kinase II phosphorylation sites at T-48, S-154, T-197, S-204, S-246, S-252, S-285, and S-385; and two potential protein kinase C phosphorylation sites at S-357, and at T-371. There is a potential prokaryotic membrane lipoprotein attachment site between L-180 and C-190. As shown in FIGS. 3A and 3B, ECMP-1 has chemical and structural homology with human S1-5 gene product (GI 458228; SEQ ID NO:5). In particular, ECMP-1 shares 53% identity, an EGF-like tandem repeat motif, and potential N-hydroxylation sites with human S1-5 gene product. Northern analysis shows the expression of this sequence in various libraries, at least 20% of which are immortalized or cancerous and at least 28% of which involve the immune response.

Nucleic acids encoding the ECMP-2 of the present invention were first identified in incyte Clone 1621777 from the brain tumor tissue cDNA library (BRAITUT13) using a computer search for amino acid sequence alignments. A consensus sequence, SEQ ID NO:4, was derived from the following overlapping and/or extended nucleic acid sequences: Incyte Clones 1621777 (BRAITUT13), 865787 (BRAITUT03), 1867044 (SKINBIT01), 1901493 (BLADTUT06) and 1957753 (CONNNOT01).

In another embodiment, the invention encompasses a polypeptide comprising the amino acid sequence of SEQ ID NO:3, as shown in FIGS. 2A–2E. ECMP-2 is 540 amino acids in length and has six potential cysteine repeats of single cysteines and cysteine doublets between C-181 and C-498. These repeats are characteristic of domains in the serum albumin family of proteins (Soltysik-Espanola, supra). There is a potential N-terminal signal peptide between M-1 and A-20 and two internal homology domains between C-151 to Y-279 and C-284 to Y-405. In addition, ECMP-2 has three potential N-glycosylation sites at N-354, N-444, and N-530; five potential casein kinase II phosphorylation sites at residues S-138, S-293, T-391, S-490, and S-533; five potential protein kinase C phosphorylation sites at T-4, T-227, S-250, T-358, and T-446; and one potential tyrosine kinase phosphorylation site at Y-374.

As shown in FIGS. 4A–4C, ECMP-2 has chemical and structural homology with the secreted protein encoded by the murine Ecm1 gene (GI 496120; SEQ ID NO:6). In particular, ECMP-2 shares 84% identity with mouse secreted protein. Both proteins share the single cysteine and cysteine doublet repeat domains. They share two of the potential N-glcosylation sites, three of the potential casein kinase II sites, and four of the potential protein kinase C sites. They also share the two internal sequence homology domains of Ecm1. Northern analysis shows the expression of this sequence in various libraries, at least 32% of which are immortalized or cancerous and at least 39% of which involve the immune response.

The invention also encompasses ECMP variants. A preferred ECMP variant is one having at least 80%, and more preferably 90%, amino acid sequence identity to the ECMP amino acid sequence (SEQ ID NO:1, or SEQ ID NO:3) and which retains at least one of the biological, structural or other functional characteristics of ECMP. A most preferred ECMP variant is one having at least 95% amino acid sequence identity to SEQ ID NO:1, or SEQ ID NO:3.

The invention also encompasses polynucleotides which encode ECMP. Accordingly, any nucleic acid sequence which encodes the amino acid sequence of ECMP can be used to produce recombinant molecules which express ECMP. In a particular embodiment, the invention encompasses the polynucleotide comprising the nucleic acid sequence of SEQ ID NO:2 or SEQ ID NO:4 as shown in FIGS. 1A–1G and FIGS. 2A–2E, respectively.

It will be appreciated by those skilled in the art that as a result of the degeneracy of the genetic code, a multitude of nucleotide sequences encoding ECMP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring ECMP, and all such variations are to be considered as being specifically disclosed.

Although nucleotide sequences which encode ECMP and its variants are preferably capable of hybridizing to the nucleotide sequence of the naturally occurring ECMP under appropriately selected conditions of stringency, it may be advantageous to produce nucleotide sequences encoding ECMP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding ECMP and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode ECMP and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding ECMP or any fragment thereof.

Also encompassed by the invention are polynucleotide sequences that are capable of hybridizing to the claimed nucleotide sequences, and in particular, those shown in SEQ ID NO:2, or SEQ ID NO:4, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE, Taq DNA polymerase, thermostable T7 polymerase (Amersham Pharmacia Biotech (APB), Piscataway, N.J.), or combinations of polymerases and proofreading exonucleases such as those found in the ELONGASE amplification system (Life Technologies, Gaithersburg, Md.). Preferably, the process is automated with machines such as the MICROLAB 2200 system (Hamilton, Reno, Nev.), DNA ENGINE thermal cycler (MJ Research, Watertown, Mass.) and ABI CATALYST and ABI PRISM 373 and 377 sequencing systems (PE Biosystems).

The nucleic acid sequences encoding ECMP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 primer analysis software (National Biosciences, Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR and nested primers to walk genomic DNA. This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR software, PE Biosystems) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode ECMP may be used in recombinant DNA molecules to direct expression of ECMP, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express ECMP.

As will be understood by those of skill in the art, it may be advantageous to produce ECMP-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter ECMP encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding ECMP may be ligated to a heterologous sequence to encode a fusion protein. For example, to screen peptide libraries for inhibitors of ECMP activity, it may be useful to encode a chimeric ECMP protein that can be recognized by a commercially available antibody. A fusion protein may also be engineered to contain a cleavage site located between the ECMP encoding sequence and the heterologous protein sequence, so that ECMP may be cleaved and purified away from the heterologous moiety.

In another embodiment, sequences encoding ECMP may be synthesized, in whole or in part, using chemical methods well known in the art (Caruthers, M. H. et al. (1980) Nucleic Acids Symp. Ser. (7) 215–223; Horn, T. et al. (1980) Nucleic Acids Symp. Ser. (7) 225–232). Alternatively, the protein itself may be produced using chemical methods to synthesize the amino acid sequence of ECMP, or a fragment thereof. For example, peptide synthesis can be performed using various solid-phase techniques (Roberge, J. Y. et al. (1995) Science 269:202–204) and automated synthesis may be achieved, for example, using the ABI 431A peptide synthesizer (PE Biosystems).

The newly synthesized peptide may be substantially purified by preparative high performance liquid chromatography (e.g., Creighton, T. (1983) *Proteins, Structures and Molecular Principles*, W H Freeman, New York, N.Y.). The composition of the synthetic peptides may be confirmed by amino acid analysis or sequencing (e.g., the Edman degradation procedure; Creighton, supra). Additionally, the amino acid sequence of ECMP, or any part thereof, may be altered during direct synthesis and/or combined using chemical methods with sequences from other proteins, or any part thereof, to produce a variant polypeptide.

In order to express a biologically active ECMP, the nucleotide sequences encoding ECMP or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding ECMP and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and in Ausubel, F. M. et al. (1989) *Current Protocols in Molecular Biology*, John Wiley & Sons, New York, N.Y.

A variety of expression vector/host systems may be utilized to contain and express sequences encoding ECMP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Life Technologies) and the like may be used. The baculovirus poly-hedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding ECMP, vectors based on SV40 or EBV may be used with an appropriate selectable marker.

In bacterial systems, a number of expression vectors may be selected depending upon the use intended for ECMP. For example, when large quantities of ECMP are needed for the induction of antibodies, vectors which direct high level expression of fusion proteins that are readily purified may be used. Such vectors include, but are not limited to, the multifunctional $E.$ $coli$ cloning and expression vectors such as BLUESCRIPT phagemid (Stratagene), in which the sequence encoding ECMP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. PGEX vectors (APB) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, $Saccharomyces$ $cerevisiae$, a number of vectors containing constitutive or inducible promoters such as alpha factor, alcohol oxidase, and PGH may be used. For reviews, see Ausubel (supra) and Grant et al. (1987) Methods Enzymol. 153:516–544.

In cases where plant expression vectors are used, the expression of sequences encoding ECMP may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (cf. Hobbs, S. or Murry, L. E. in $Yearbook$ $of$ $Science$ $and$ $Technology$ (1992) McGraw Hill, New York, N.Y.; pp. 191–196).

An insect system may also be used to express ECMP. For example, in one such system, $Autographa$ $californica$ nuclear polyhedrosis virus (AcNPV) is used as a vector to express foreign genes in $Spodoptera$ $frugiperda$ cells or in $Trichoplusia$ larvae. The sequences encoding ECMP may be cloned into a non-essential region of the virus, such as the polyhedrin gene, and placed under control of the polyhedrin promoter. Successful insertion of ECMP will render the polyhedrin gene inactive and produce recombinant virus lacking coat protein. The recombinant viruses may then be used to infect, for example, $S.$ $frugiperda$ cells or $Trichoplusia$ larvae in which ECMP may be expressed (Engelhard, E. K. et al. (1994) Proc. Natl. Acad. Sci. 91:3224–3227).

In mammalian host cells, a number of viral-based expression systems may be utilized. In cases where an adenovirus is used as an expression vector, sequences encoding ECMP may be ligated into an adenovirus transcription/translation complex consisting of the late promoter and tripartite leader sequence. Insertion in a non-essential E1 or E3 region of the viral genome may be used to obtain a viable virus which is capable of expressing ECMP in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding ECMP. Such signals include the ATG initiation codon and adjacent sequences. In cases where sequences encoding ECMP, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for posttranslational activities (e.g., CHO, HeLa, MDCK, HEK293, and WI38), are available from the American Type Culture Collection (ATCC; Manassas, Va.) and may be chosen to ensure the correct modification and processing of the foreign protein.

For long-term, high-yield production of recombinant proteins, stable expression is preferred. For example, cell lines which stably express ECMP may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–232) and adenine phosphoribosyltransferase (Lowy, I. et al. (1980) Cell 22:817–823) genes which can be employed in tk or aprt cells, respectively. Also, antimetabolite, antibiotic or herbicide resistance can be used as the basis for selection; for example, dhfr, which confers resistance to methotrexate (Wigler, M. et al. (1980) Proc. Natl. Acad. Sci. 77:3567–3570); npt, which confers resistance to the aminoglycosides, neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–8051). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding ECMP is inserted within a marker gene sequence, transformed cells containing sequences encoding ECMP can be identified by the absence of marker gene function. Alternatively, a marker gene can be placed in tandem with a sequence encoding ECMP under the control of a single promoter. Expression of the marker gene in response to induction or selection usually indicates expression of the tandem gene as well.

Alternatively, host cells which contain the nucleic acid sequence encoding ECMP and express ECMP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding ECMP can be detected by DNA-DNA or DNA-RNA hybridization or amplification using probes or fragments or fragments of polynucleotides encoding ECMP. Nucleic acid amplification based assays involve the use of oligonucleotides or oligomers based on the sequences encoding ECMP to detect transformants containing DNA or RNA encoding ECMP.

A variety of protocols for detecting and measuring the expression of ECMP, using either polyclonal or monoclonal antibodies specific for the protein are known in the art. Examples include enzyme-linked immunosorbent assay (ELISA), radioimmunoassay (RIA), and fluorescence activated cell sorting (–). A two-site, monoclonal-based immunoassay utilizing monoclonal antibodies reactive to two non-interfering epitopes on ECMP is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding ECMP include oligolabeling, nick translation, end-labeling or PCR amplification using a labeled nucleotide. Alternatively, the sequences encoding ECMP, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (APB; Promega, Madison, Wis.). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding ECMP may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode ECMP may be designed to contain signal sequences which direct secretion of ECMP through a prokaryotic or eukaryotic cell membrane. Other constructions may be used to join sequences encoding ECMP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex, Seattle, Wash.). The inclusion of cleavable linker sequences such as those specific for Factor XA or enterokinase (Invitrogen, San Diego, Calif.) between the purification domain and ECMP may be used to facilitate purification. One such expression vector provides for expression of a fusion protein containing ECMP and a nucleic acid encoding 6 histidine residues preceding a thioredoxin or an enterokinase cleavage site. The histidine residues facilitate purification on IMAC (immobilized metal ion affinity chromatography) as described in Porath, J. et al.

(1992, Prot. Exp. Purif. 3:263–281) while the enterokinase cleavage site provides a means for purifying ECMP from the fusion protein. A discussion of vectors which contain fusion proteins is provided in Kroll, D. J. et al. (1993; DNA Cell Biol. 12:441–453).

In addition to recombinant production, fragments of ECMP may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using ABI 431A peptide synthesizer (PE Biosystems). Various fragments of ECMP may be chemically synthesized separately and combined using chemical methods to produce the full length molecule.

THERAPEUTICS

Chemical and structural homology exits among ECMP-1 and human S1-5 gene product (GI 458228). In addition, ECMP-1 is expressed in tissues associated with cancer and the immune response. Therefore, ECMP-1 appears to play a role in cancer and immune disorders, particularly disorders in which ECMP-1 is overexpressed.

Therefore, in one embodiment, an antagonist of ECMP-1 may be administered to a subject to prevent or treat cancer. Cancers may include, but are not limited to adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector expressing the complement of the polynucleotide encoding ECMP-1 may be administered to a subject to treat or prevent cancer including, but not limited to, the types of cancer described above.

In another embodiment, an antagonist of ECMP-1 may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, Werner syndrome, and autoimmune thyroiditis; complications of cancer, hemodialysis, extracorporeal circulation; viral, bacterial, fungal, parasitic, protozoal, and helminthic infections and trauma.

In another embodiment, a vector expressing the complement of the polynucleotide encoding ECMP-1 may be administered to a subject to treat or prevent an immune disorder including, but not limited to, those described above.

In one aspect, antibodies which specifically bind ECMP-1 may be used directly as an antagonist or indirectly as a targeting or delivery mechanism for bringing a pharmaceutical agent to cells or tissue which express ECMP-1.

Chemical and structural homology exits among ECMP-2 and murine secreted protein encoded by Ecm1 gene (GI 496120). In addition, ECMP-2 is expressed in tissues associated with cancer and the immune response. Therefore, ECMP-2 appears to play a role in cancer and immune disorders, particularly disorders in which ECMP-2 is overexpressed.

Therefore, in another embodiment, an antagonist of ECMP-2 may be administered to a subject to prevent or treat cancer. Cancers may include, but are not limited to, adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector expressing the complement of the polynucleotide encoding ECMP-2 may be administered to a subject to treat or prevent a cancer including, but not limited to, any of the types of cancer described above.

In another embodiment, an antagonist of ECMP-2 may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, Werner syndrome, and autoimmune thyroiditis; complications of cancer, hemodialysis, extracorporeal circulation; viral, bacterial, fungal, parasitic, protozoal, and helminthic infections and trauma.

In another embodiment, a vector expressing the complement of the polynucleotide encoding ECMP-2 may be administered to a subject to treat or prevent an immune disorder including, but not limited to, those described above.

In one aspect, an antibody which specifically binds ECMP-2 may be used directly as an antagonist or indirectly as a targeting or delivery mechanism for bringing a pharmaceutical agent to cells or tissue which express ECMP-2.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of ECMP may be produced using methods which are generally known in the art. In particular, purified ECMP may be used to produce antibodies or to screen libraries of pharmaceutical agents to identify those which specifically bind ECMP.

Antibodies to ECMP may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with ECMP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to ECMP have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of ECMP amino acids may be fused with those of another protein such as keyhole limpet hemocyanin and antibody produced against the chimeric molecule.

Monoclonal antibodies to ECMP may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce ECMP-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:10134–10137).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for ECMP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between ECMP and its specific antibody. A two-site, monoclonal-based immunoassay utilizing monoclonal antibodies reactive to two non-interfering ECMP epitopes is preferred, but a competitive binding assay may also be employed (Maddox, supra).

In another embodiment of the invention, the polynucleotides encoding ECMP, or any fragment or complement thereof, may be used for therapeutic purposes. In one aspect, the complement of the polynucleotide encoding ECMP may be used in situations in which it would be desirable to block the transcription of the MRNA. In particular, cells may be transformed with sequences complementary to polynucleotides encoding ECMP. Thus, complementary molecules or fragments may be used to modulate ECMP activity, or to achieve regulation of gene function. Such technology is now well known in the art, and sense or antisense oligonucleotides or larger fragments, can be designed from various locations along the coding or control regions of sequences encoding ECMP.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding ECMP. These techniques are described both in Sambrook (supra) and in Ausubel (supra).

Genes encoding ECMP can be turned off by transforming a cell or tissue with expression vectors which express high levels of a polynucleotide or fragment thereof which encodes ECMP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding ECMP (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing, Mt. Kisco, N.Y.). The complementary sequence or antisense molecule may also be designed to block translation of MRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding ECMP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding ECMP. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–466; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of ECMP, antibodies to ECMP, mimetics, agonists, antagonists, or inhibitors of ECMP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing, Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of ECMP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans. A therapeutically effective dose refers to that amount of active ingredient, for example ECMP or fragments thereof, antibodies of ECMP, agonists, antagonists or inhibitors of ECMP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind ECMP may be used for the diagnosis of conditions or disorders characterized by expression of ECMP, or in assays to monitor patients being treated with ECMP, agonists, antagonists or inhibitors. The antibodies useful for diagnostic purposes may be prepared in the same manner as those described above for therapeutics. Diagnostic assays for ECMP include methods which utilize the antibody and a label to detect ECMP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring ECMP are known in the art and provide a basis for diagnosing altered or abnormal levels of ECMP expression. Normal or standard values for ECMP expression are established by combining body fluids or cell extracts taken from normal mammalian subjects, preferably human, with antibody to ECMP under conditions suitable for complex formation. The amount of standard complex formation may be quantified by various methods, but preferably by photometric, means. Quantities of ECMP expressed in subject, control and disease, samples from biopsied tissues are compared with the standard values. Deviation between standard and subject values establishes the parameters for diagnosing disease.

In another embodiment of the invention, the polynucleotides encoding ECMP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of ECMP may be correlated with disease. The diagnostic assay may be used to distinguish between absence, presence, and excess expression of ECMP, and to monitor regulation of ECMP levels during therapeutic intervention.

In one aspect, hybridization with PCR probes which are capable of detecting polynucleotide sequences, including genomic sequences, encoding ECMP or closely related molecules, may be used to identify nucleic acid sequences which encode ECMP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding ECMP, alleles, or related sequences.

Probes may also be used for the detection of related sequences, and should preferably contain at least 50% of the nucleotides from any of the ECMP encoding sequences. The hybridization probes of the subject invention may be DNA or RNA and derived from the nucleotide sequence of SEQ ID NO:2, or SEQ ID NO:4 or from genomic sequence including promoter, enhancer elements, and introns of the naturally occurring ECMP.

Means for producing specific hybridization probes for DNAs encoding ECMP include the cloning of nucleic acid sequences encoding ECMP or ECMP derivatives into vectors for the production of MRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding ECMP may be used for the diagnosis of conditions, or disorders which are associated with expression of ECMP. Examples of such conditions or diseases include cancer such as cancer of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; immune disorders such as AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, Werner syndrome, and autoimmune thyroiditis; complications of cancer, hemodialysis, extracorporeal circulation; viral, bacterial, fungal, parasitic, protozoal, and helminthic infections and trauma. The polynucleotide sequences encoding ECMP may be used in Southern or northern analysis, dot blot, or other membrane-based technologies; in PCR technologies; or in dipstick, pin, ELISA-like assays or microarrays utilizing fluids or tissues from patient biopsies to detect altered ECMP expression. Such qualitative or quantitative methods are well known in the art.

In a particular aspect, the nucleotide sequences encoding ECMP may be useful in assays that detect activation or induction of various cancers, particularly those mentioned above. The nucleotide sequences encoding ECMP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding ECMP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of ECMP, a normal or standard profile for expression is established. This may be accomplished by combining body fluids or cell extracts taken from normal subjects, either animal or human, with a sequence, or a fragment thereof, which encodes ECMP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding ECMP may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of ECMP include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:229–236). The speed of quantitation of multiple samples may be accelerated by running the assay in an ELISA-like format where the oligomer of interest is presented in various dilutions and a spectrophotometric or colorimetric response gives rapid quantitation.

In further embodiments, oligonucleotides derived from any of the polynucleotide sequences described herein may be used as targets in microarrays. The microarrays can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–2155).

In one embodiment, the microarray is prepared and used according to the methods described in PCT application WO95/11995 (Chee et al.), Lockhart, D. J. et al. (1996; Nat. Biotech. 14:1675–1680) and Schena, M. et al. (1996; Proc. Natl. Acad. Sci. 93:10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, the oligomers may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array may be produced by hand or using available devices (slot blot or dot blot apparatus), materials (any suitable solid support), and machines (including robotic instruments) and may contain 8, 24, 96, 384, 1536 or 6144 oligonucleotides, or any other multiple between two and one million which lends itself to the efficient use of commercially available instrumentation.

In order to conduct sample analysis using the microarrays, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode ECMP may also be used to generate hybridization probes which are useful for mapping the naturally occurring genomic sequence. The sequences may be mapped to a particular chromosome, to a specific region of a chromosome or to artificial chromosome constructions, such as human artificial chromosomes, yeast artificial chromosomes, bacterial artificial chromosomes, bacterial P1 constructions or single chromosome cDNA libraries (Price, C. M. (1993) Blood Rev. 7:127–134; Trask, B. J. (1991) Trends Genet. 7:149–154).

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding ECMP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, ECMP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between ECMP and the agent being tested, may be measured.

Another technique for drug screening which may be used provides for high throughput screening of compounds having suitable binding affinity to the protein of interest as described in published PCT application WO84/03564. In this method, as applied to ECMP large numbers of different small test compounds are synthesized on a solid substrate, such as plastic pins or some other surface. The test compounds are reacted with ECMP, or fragments thereof, and washed. Bound ECMP is then detected by methods well known in the art. Purified ECMP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding ECMP specifically compete with a test compound for binding ECMP. In this manner, the antibodies can be used to detect the presence of any peptide which shares one or more antigenic determinants with ECMP.

In additional embodiments, the nucleotide sequences which encode ECMP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction
CORNNOT01

The corneal fibroblast CORNNOT01 cDNA library was custom constructed by Stratagene using stromal RNA isolated from the corneal fibroblasts of a 76-year-old. Stratagene prepared the cDNA library using an XhoI-oligo d(T) primer. Double-stranded cDNA was blunted, ligated to EcoRI adaptors, digested with XhoI, size-selected, and cloned into the XhoI and EcoRI sites of the Lambda UNI-ZAP vector (Stratagene). Following packaging, $2\times10^6$ primary clones were amplified to stabilize the library for long-term storage.

The quality of the cDNA library was screened using DNA probes, and then, the BLUESCRIPT phagemid (Stratagene) was excised. Subsequently, the custom-constructed library phage particles were infected into E. coli host strain XL1-BLUE (Stratagene). Alternative unidirectional vectors include, but are not limited to, PCDNA1 (Invitrogen) and PSHLOX-1 (Novagen, Madison Wis.).

BRAITUT13

The brain tumor BRAITUT13 cDNA library was constructed from cancerous brain tissue obtained from a 68-year-old Caucasian male (specimen #0370) during cerebral meningeal excision following diagnosis of meningioma localized in the left frontal part of the brain. In a prior surgery the patient had undergone a replacement of aortic valve with tissue graft.

The frozen tissue was homogenized and lysed using a POLYTRON homogenizer (PT-3000; Brinkmann Instruments, Westbury, N.J.) in guanidinium isothiocyanate solution. The lysate was centrifuged over a 5.7 M CsCl cushion using an SW28 rotor in an L8-70M ultracentrifuge (Beckman Coulter, Fullerton, Calif.) for 18 hours at 25,000 rpm at ambient temperature. The RNA was extracted with acid phenol, pH 4.7, precipitated using 0.3 M sodium acetate and 2.5 volumes of ethanol, resuspended in RNAse-free water, and treated with DNase at 37° C. Extraction and precipitation were repeated as before. The mRNA was isolated with the OLIGOTEX kit (Qiagen, Chatsworth, Calif.) and used to construct the cDNA library.

The mRNA was handled according to the recommended protocols in the SUPERSCRIPT plasmid system (Life Technologies). cDNAs were fractionated on a SEPHAROSE CL4B column (APB), and those cDNAs exceeding 400 bp were ligated into PSPORT1 plasmid (Life Technologies). The plasmid was subsequently transformed into DH5α competent cells (Life Technologies).

II Isolation and Sequencing of cDNA Clones
CORNNOT01

The phagemid forms of individual cDNA clones were obtained by the in vivo excision process, in which the host bacterial strain, XL1-BLUE (Stratagene) was coinfected with both the lambda library phage and an f1 helper phage (Stratagene). Polypeptides or enzymes derived from both the library-containing phage and the helper phage nicked the DNA, initiating new DNA synthesis from defined sequences on the target DNA and creating a smaller, single stranded circular phagemid DNA molecule that included all DNA, sequences of the PBLUESCRIPT phagemid and the cDNA insert. The phagemid DNA was released from the cells and purified, then used to re-infect fresh host cells (SOLR, Stratagene) where the double stranded DNA was produced. Because the phagemid carries the gene for β-lactamase, the newly-transformed bacteria were selected on medium containing ampicillin.

Phagemid DNA was purified using the QIAWELL-8 plasmid, QIAWELL PLUS, or QIAWELL ULTRA DNA purification systems (Qiagen). An alternative method for purifying the phagemid utilizes the MINIPREP kit (Edge Biosystems, Gaithersburg, Md.).

BRAITUT13

Plasmid DNA was released from the cells and purified using the REAL PREP 96 plasmid kit (Qiagen). The recommended protocol was employed except for the following changes: 1) the bacteria were cultured in 1 ml of sterile Terrific Broth (Life Technologies) with carbenicillin (Carb) at 25 mg/l and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using MICROLAB 2200 system (Hamilton) in combination with DNA ENGINE thermal cyclers (MJ Research) and sequenced using ABI PRISM 377 sequencing systems (PE Biosystems).

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul, S. F. (1993) J. Mol. Evol. 36:290–300; Altschul et al. (1990) J. Mol. Biol. 215:403–410).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R. F. and T. F. Smith (1992; Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin, S. and S. F. Atschul (1993; Proc. Natl. Acad. Sci. 90:5873–5877) and incorporated herein by reference, searches for matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and mammalian sequences (mam), and deduced amino acid sequences from the same clones are searched against GenBank functional protein databases, mammalian (mamp), vertebrate (vrtp) and eukaryote (eukp), for homology. The relevant database for a particular match were reported as a GIxxx±p (where xxx is pri, rod, etc and if present, p=peptide).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook, supra).

Analogous computer techniques using BLAST (Altschul, supra) are used to search for identical or related molecules in nucleotide databases such as GenBank or the LIFESEQ database (Incyte Pharmaceuticals, Palo Alto, Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximumBLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding ECMP occurs. Abundance and percent abundance are also reported. Abundance directly reflects the number of times a particular transcript is represented in a cDNA library, and percent abundance is abundance divided by the total number of sequences examined in the cDNA library.

V Extension of ECMP Encoding Polynucleotides

The nucleic acid sequence of the Incyte Clone 45517 or 162177 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 primer analysis software (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Life Technologies) were used to extend the sequence. If more than one extension is necessary or desired, additional sets of primers are designed to further extend the known region.

High fidelity amplification was obtained by following the instructions for the XL-PCR kit (PE Biosystems) and thoroughly mixing the enzyme and reaction mix. Beginning with 40 pmol of each primer and the recommended concentrations of all other components of the kit, PCR was performed using the DNA ENGINE thermal cycler (MJ Research) and the following parameters:

| Step | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK kit (Qiagen), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent E. coli cells (in 40 μl of appropriate media) were transformed with 3 μl of ligation mixture and cultured in 80 μl of SOC medium (Sambrook, supra). After incubation for one hour at 37° C., the E. coli mixture was plated on Luria Bertani (LB)-agar (Sambrook, supra) containing 2x Carb. The following day, several colonies were randomly picked from each plate and cultured in 150 μl of liquid LB/2x Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3x) containing 4 units of rTth DNA polymerase (PE Biosystems), a vector primer, and one or both of the gene specific primers used for the extension reaction were added to each well. Amplification was performed using the following conditions:

| Step 1 | 94° C. for 60 sec |
|---|---|
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2, or SEQ ID NO:4, is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2, or SEQ ID NO:4 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 primer analysis software (National Biosciences), labeled by combining 50 pmol of each oligomer and 250 $\mu$Ci of [$\gamma$-$^{32}$P] adenosine triphosphate (APB) and T4 polynucleotide kinase (NEN Life Science Products, Boston, Mass.). The labeled oligonucleotides are substantially purified with SEPHADEX G-25 superfine resin column (APB). A aliquot containing $10^7$ counts per minute of the labeled probe is used in a typical membrane-based hybridization analysis of human genomic DNA digested with one of the following endonucleases—Ase I, Bgl II, Eco RI, Pst I, Xba 1, or Pvu II (NEN Life Science Products).

The DNA from each digest is fractionated on a 0.7 percent agarose gel and transferred to nylon membranes (NYTRANPLUS, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR film (Eastman Kodak, Rochester, N.Y.) is exposed to the blots in a PHOSPHORIMAGER cassette (APB), hybridization patterns are compared.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al. PCT/WO95/11995, incorporated herein by reference).

In the alternative, a chemical coupling procedure and an ink jet device are used to synthesize oligomers on the surface of a substrate (Baldeschweiler, J. D. et al. PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the ECMP-encoding sequence, or any part thereof, is used to decrease or inhibit expression of naturally occurring ECMP. Although use of oligonucleotides comprising from about 15 to about 30 base-pairs is described, essentially the same procedure is used with smaller or larger sequence fragments. Appropriate oligonucleotides are designed using OLIGO 4.06 primer analysis software (National Biosciences) and the coding sequence of ECMP, SEQ ID NO:1, or SEQ ID NO:3. To inhibit transcription, a complementary oligonucleotide is designed from the most unique 5' sequence and used to prevent promoter binding to the coding sequence. To inhibit translation, a complementary oligonucleotide is designed to prevent ribosomal binding to the ECMP-encoding transcript.

IX Expression of ECMP

Expression of ECMP is accomplished by subcloning the cDNAs into appropriate vectors and transforming the vectors into host cells. In this case, the cloning vector is also used to express ECMP in E. coli. Upstream of the cloning site, this vector contains a promoter for $\beta$-galactosidase, followed by sequence containing the amino-terminal Met, and the subsequent seven residues of $\beta$-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of $\beta$-galactosidase, about 5 to 15 residues of linker, and the full length protein. The signal residues direct the secretion of ECMP into the bacterial growth media which can be used directly in the following assay for activity.

X Demonstration of ECMP Activity

The activity of ECMP-1 and ECMP-2 may be measured using an assay based upon the property of ECMPs to support proliferation in vitro of fibroblasts and tumor cells under serum-free conditions (Chiquet-Ehrismann, R. et al. (1986) Cell 47:131–139). Wells in 96 well cluster plates (Falcon, Fisher Scientific, Santa Clara, Calif.) are coated with ECMP by incubation with solutions at 50–100 $\mu$g/ml for 15 min at ambient temperature. The coating solution is aspirated, and the wells washed with Dulbecco's medium before cells are plated. Rat fibroblast cultures or rat mammary tumor cells are prepared as described and plated at a density of $10^4$–$10^5$ cells/ml in Dulbecco's medium supplemented with 10% fetal calf serum.

After three days the media are removed, and the cells washed three times with phosphate-buffered saline (PBS) before the addition of serum-free Dulbecco's medium containing 0.25 mg/ml bovine serum albumin (BSA, Fraction V, Sigma-Aldrich, St. Louis, Mo.). After 2 days the medium is aspirated, and 100 μl of [3H]thymidine (NEN Life Sciences Products) at 2 μCi/ml in fresh Dulbecco's medium containing 0.25 mg/ml BSA added. Parallel plates are fixed and stained to determine cell numbers. After 16 hr, the medium is aspirated, the cell layer washed with PBS, and the 10% trichloroacetic acid-precipitable counts in the cell layer determined by liquid scintillation counting of radioisotope (normalized to relative cell numbers; Chiquet-Ehrismann supra).

XI Production of ECMP Specific Antibodies

ECMP that is substantially purified using PAGE electrophoresis (Sambrook, supra), or other purification techniques, is used to immunize rabbits and to produce antibodies using standard protocols. The amino acid sequence deduced from SEQ ID NO:2, or SEQ ID NO:4 is analyzed using LASERGENE software (DNASTAR) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel (supra), and others.

Typically, the oligopeptides are 15 residues in length, synthesized using an ABI 431A peptide synthesizer (PE Biosystems) using Fmoc-chemistry, and coupled to keyhole limpet hemocyanin (KLH, Sigma -Aldrich) by reaction with N-maleimidobenzoyl-N-hydroxysuccinimide ester (Ausubel, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio-iodinated, goat anti-rabbit IgG.

XII Purification of Naturally Occurring ECMP Using Specific Antibodies

Naturally occurring or recombinant ECMP is substantially purified by immunoaffinity chromatography using antibodies specific for ECMP. An immunoaffinity column is constructed by covalently coupling ECMP antibody to an activated chromatographic resin, such as CNBr-activated SEPHAROSE (APB). After the coupling, the resin is blocked and washed according to the manufacturer's instructions.

Media containing ECMP is passed over the immunoaffinity column, and the column is washed under conditions that allow the preferential absorbance of ECMP (e.g., high ionic strength buffers in the presence of detergent). The column is eluted under conditions that disrupt antibody/ECMP binding (e.g., a buffer of pH 2–3 or a high concentration of a chaotrope, such as urea or thiocyanate ion), and ECMP is collected.

XIII Identification of Molecules Which Interact with ECMP

ECMP or biologically active fragments thereof are labeled with $^{125}$I Bolton-Hunter reagent (Bolton et al. (1973) Biochem. J. 133:529–539). Candidate molecules previously arrayed in the wells of a multi-well plate are incubated with the labeled ECMP, washed and any wells with labeled ECMP complex are assayed. Data obtained using different concentrations of ECMP are used to calculate values for the number, affinity, and association of ECMP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated polynucleotide encoding a protein comprising the amino acid sequence of SEQ ID NO:3.

2. A composition comprising the polynucleotide of claim 1.

3. A polynucleotide which hybridizes to the full length of the polynucleotide of claim 1.

4. A polynucleotide which is fully complementary to the polynucleotide of claim 1.

5. An isolated polynucleotide comprising SEQ ID NO:4.

6. A composition comprising the polynucleotide of claim 5.

7. A polynucleotide which is full complementary to the polynucleotide of claim 5.

8. An expression vector containing the polynucleotide of claim 1.

9. A host cell containing the vector of claim 8.

10. A method for producing a protein comprising the amino acid sequence of SEQ ID NO:3, the method comprising the steps of:
    a) culturing the host cell of claim 9 under conditions for the expression of the protein; and
    b) recovering the protein from the host cell culture.

11. A method for detecting a polynucleotide which encodes the protein of SEQ ID NO:3 in a biological sample comprising the steps of:
    a) hybridizing the polynucleotide of claim 4 to nucleic acid material of a biological sample, thereby forming a hybridization complex; and
    b) detecting said hybridization complex, wherein the presence of said complex correlates with the presence of a polynucleotide encoding the protein in said biological sample.

12. The method of claim 11 wherein the nucleic acid material is amplified by the polymerase chain reaction prior to hybridization.

13. A method of using a polynucleotide to screen a library of molecules to identify at least one molecule which specifically binds the polynucleotide, the method comprising the steps of:
    a) combining the polynucleotide of claim 1 with a library of molecules under conditions to allow specific binding, and
    b) detecting specific binding, thereby identifying a molecule which specifically binds the polynucleotide.

14. The method of claim 13 wherein the library is selected from DNA molecules, RNA molecules, peptide nucleic acids, transcription factors, and artificial chromosome constructions.

15. A method of using a polynucleotide to purify a molecule which specifically binds the polynucleotide from a sample, the method comprising:
    a) combining the polynucleotide of claim 1 with a sample under conditions to allow specific binding;
    b) recovering the bound polynucleotide; and
    c) separating the polynucleotide from the molecule, thereby obtaining a purified molecule.

* * * * *

UNITED STATES PATENT AND TRADEMARK OFFICE
CERTIFICATE OF CORRECTION

PATENT NO. : 6,303,765 B1 Page 1 of 1
DATED : October 16, 2001
INVENTOR(S) : Bandman et al.

It is certified that error appears in the above-identified patent and that said Letters Patent is hereby corrected as shown below:

<u>Column 53,</u>
Line 41, please replace, "full," with -- fully --.

Signed and Sealed this

Twenty-seventh Day of August, 2002

*Attest:*

JAMES E. ROGAN
*Attesting Officer* *Director of the United States Patent and Trademark Office*